United States Patent
Regeimbal et al.

(10) Patent No.: US 11,224,626 B2
(45) Date of Patent: Jan. 18, 2022

(54) METHODS OF IDENTIFYING BACTERIOPHAGES THAT CAN INFECT AND KILL HOST-ADAPTED INFECTIOUS PATHOGENIC BACTERIA

(71) Applicants: James M Regeimbal, Washington's Crossing, PA (US); Stuart D Tyner, Great Falls, VA (US)

(72) Inventors: James M Regeimbal, Washington's Crossing, PA (US); Stuart D Tyner, Great Falls, VA (US)

(73) Assignees: The United States of America as Represented by the Secretary of the Navy, Arlington, VA (US); The United States of America as Represented by the Secretary of the Army, Silver Spring, MD (US)

( * ) Notice: Subject to any disclaimer, the term of this patent is extended or adjusted under 35 U.S.C. 154(b) by 167 days.

(21) Appl. No.: 16/112,148

(22) Filed: Aug. 24, 2018

(65) Prior Publication Data
US 2019/0060380 A1     Feb. 28, 2019

Related U.S. Application Data

(60) Provisional application No. 62/550,461, filed on Aug. 25, 2017.

(51) Int. Cl.
*C12N 7/00*        (2006.01)
*A61K 35/76*     (2015.01)

(52) U.S. Cl.
CPC .............. *A61K 35/76* (2013.01); *C12N 7/00* (2013.01); *C12N 2795/00032* (2013.01); *C12N 2795/00051* (2013.01)

(58) Field of Classification Search
CPC .............. A61K 35/76; C12N 7/00; C12N 2795/00032; C12N 2795/00051
See application file for complete search history.

(56) References Cited

U.S. PATENT DOCUMENTS

| | | | |
|---|---|---|---|
| 2006/0094076 A1 | 5/2006 | Stave et al. | |
| 2014/0273159 A1 | 9/2014 | Summer et al. | |
| 2015/0017629 A1 | 1/2015 | Derda et al. | |
| 2016/0310549 A1* | 10/2016 | Appaiah | C12N 1/20 |
| 2017/0035077 A1* | 2/2017 | Dastych | C12Q 1/18 |
| 2017/0368116 A1 | 12/2017 | Regeimbal et al. | |

FOREIGN PATENT DOCUMENTS

| | | |
|---|---|---|
| WO | 2001000786 A2 | 1/2001 |
| WO | 2017087909 A1 | 5/2017 |

OTHER PUBLICATIONS

Mattila, S. et al., On-Demand Isolation of Bacteriophages Against Drug-Resistant Bacteria for Personalized Phage Therapy, 2015, Frontiers in Microbiology, 6:1271, 1-7 (Year: 2015).*
Kawaoka, Y. et al., Growth Temperature-dependent Variation in the Bacteriophage-inactivating Capacity and Antigenicity of Yersinia enterocolitica Lipopolysaccharide, 1983, Journal of General Microbiology, 129, 2739-2747 (Year: 1983).*
Crother, T. et al., Antigenic Composition of Borrelia burgdorferi during Infection of SCID Mice, 2003, Infection and Immunity, 71(6): 3419-3428 (Year: 2003).*
International Search Report and Written Opinion for PCT/US2018/047970 dated Oct. 30, 2018.
Mattila el al., Frontiers in Microbiology, Nov. 13, 2015, vol. 6, Article 1271, pp. 1-7.
Melnikow el al., Veterinary Microbiology, Oct. 31, 2005, vol. 110, Nos. 3-4, pp. 255-263 (abstract).
Sillankorva et al., FEMS Microbiology Letters, Dec. 1, 2004, vol. 241, Iss. 1, pp. 13-20.
Hartstein et al., Journal of Clinical Microbiology, Aug. 31, 1989, vol. 27, No. 8, pp. 1874-1879.
Ang, S. et al. Infection and Immunity 69:1679-1686 (2001).
Boyce, J. et al. Emerg. Infect. Dis. 10:1357-1362 (2004).
Cottet, S. et al. J. Biol. Chem. 227:33978-33986 (2002).
Crother, T. et al. Infection and Immunity 71:3419-3428 (2003).
Cullen, P. et al. Infetion and Immunity 70:2311-2318 (2002).
Guina, T. et al. J. Am. Soc. Mass. Spectrom. 14:742-751 (2003).
Henry, M. et al. Bacteriophage 2:159-167 (2012).
Karita, M. et al. Infection and Immunity 64:4501-4507 (1996).
Merrell, D. et al. Infection and Immunity 71:3529-3539 (2003).
Paustian, M. et al. Infection and Immunity 69:4109-4115 (2001).
Paustian, M. et al. J. Bacteriol. 184:3734-3739 (2002).
Tremoulet, F. et al. FEMS Microbiology Letters 210:25-31 (2002).
Wu, H.J. et al. Current Opinion in Chemical Biology 12:93-101 (2008).
PowerPoint slide, "Outstanding Preclinical Questions-support to clinical trials" presented by Applicant to University of Cincinnati College of Medicine, Mar. 2, 2017.

* cited by examiner

*Primary Examiner* — Louise W Humphrey
*Assistant Examiner* — Anjali Ajit Hirani
(74) *Attorney, Agent, or Firm* — Diane Tso; Ning Yang

(57) ABSTRACT

The subject matter of the instant invention relates to methods of enhancing harvesting of phages against a targeted host bacteria, as well as methods of identifying phages likely to have an enhanced propensity to infect and kill an infectious pathogenic bacteria in vivo, from samples comprising phages. The invention also relates to phage libraries, pharmaceutical compositions, methods of treatment, and phage-based diagnostic methods and methods of detecting bacteria related thereto.

27 Claims, 14 Drawing Sheets

FIGURE 5

| Host strain | Phages | |
| --- | --- | --- |
| | without FBS | with FBS |
| KP01 | 1 | 1 |
| KP03 | 4, 3 | 4⁺, 1 |
| KP04 | 1 | 1⁺ |
| KP06 | 1⁺ | 1 |
| KP07 | 4, 4, 1 | 1⁺ |
| KP08 | 1 | 1 |
| KP09 | 1 | 6, 6 |
| KP11 | 1 | 1 |
| KP12 | 1 | 1⁺ |
| KP13 | 2 | 2, 3 |

*Klebsiella pneumoniae* (51)

| Bacterial code | Water source code | Water source name | Phage | | |
|---|---|---|---|---|---|
| | | | Only media | FBS at 37°C+Sh | SB at RT non-Sh |
| WIQ0239 | SWI002 | BE sewage waterway (inside) | 1/20 1/20 1/20 | 2/20 2/20 2/20 | 0/20 0/20 1/20 |
| WIQ0242 | SWI002 | BE sewage waterway (inside) | 1/20 1/20 2/20 | 1/20 1/20 1/20    1/20 1/20 1/20 | 1/20 1/20 1/20    1/20 1/20 1/20 |
| WIQ0247 | SWI002 | BE sewage waterway (inside) | 1/20 1/20 2/20 | 1/20 1/20 1/20    1/20 1/20 2/20 | 1/20 1/20 2/20    1/20 1/20 2/20 |
| WIQ0266 | SWI002 | BE sewage waterway (inside) | 3/20 2/20 2/20 | 2/20 1/20 1/20    2/20 2/20 0/20 | 2/20 1/20 1/20 |
| WIQ0289 | SWI002 | BE sewage waterway (inside) | 1/20 0/20 0/20 | 1/20 1/20 1/20 | 2/20 2/20 1/20    2/20 2/20 1/20 |

*KP on plates with SB grew at RT*

FIGURE 6

*Klebsiella pneumoniae* (S2)

| Bacterial code | Water source code | Water source name | Phage | | |
|---|---|---|---|---|---|
| | | | Only media | FBS at RT non-Sh | SB at 37°C+Sh |
| WIQ0290 | SWI004 | PE sewage waterway | 9/20 6/20 6/20 | No phage isolated | 8/20 4/20 6/20 |
| WIQ0311 | SWI004 | PE sewage waterway | 2/20 2/20 2/20 | 2/20 2/20 2/20 / 2/20 2/20 2/20 | 2/20 2/20 2/20 / 3/20 2/20 2/20 |
| WIQ0348 | SWI004 | PE sewage waterway | No phage isolated | No phage isolated | 7/20 4/20 8/20 |
| WIQ0350 | SWI004 | PE sewage waterway | 8/20 4/20 5/20 | 5/20 4/20 3/20 | 8/20 4/20 6/20 |
| WIQ0361 | SWI004 | PE sewage waterway | 3/20 2/20 2/20 | 1/20 1/20 1/20 / 1/20 1/20 1/20 | 1/20 1/20 1/20 / 1/20 1/20 1/20 |

KP on plates with FBS grew at RT

FIGURE 7

*Pseudomonas aeruginosa* (S3)

| Bacterial code | Water source code | Water source name | Phage | | |
|---|---|---|---|---|---|
| | | | Only media | FBS at RT non-Sh | SB at 37ºC+Sh |
| NSI1423 | SWI004 | PE sewage waterway | 7/20<br>7/20<br>7/20 | No phage isolated | 11/20  11/20<br>9/20   6/20<br>12/20  11/20 |
| NSI1477 | SWI004 | PE sewage waterway | 2/20<br>2/20<br>4/20 | No phage isolated | 11/20<br>6/20<br>12/20 |
| NSI1479 | SWI004 | PE sewage waterway | No phage isolated | No phage isolated | No phage isolated |
| NSI1485 | SWI004 | PE sewage waterway | No phage isolated | No phage isolated | No phage isolated |
| NSI1488 | SWI004 | PE sewage waterway | 15/20<br>11/20<br>16/20 | No phage isolated | 14/20  14/20<br>11/20  10/20<br>15/20  14/20 |

*PA on plates with FBS grew at RT*

FIGURE 8A

*Pseudomonas aeruginosa* (S3)

| Bacteria code | Water source code | Water source name | Phage | | |
|---|---|---|---|---|---|
| | | | Only media | FBS at RT non-Sh | SB at 37°C+Sh |
| NSI0978 | SWI002 | BE sewage waterway (outside) | 2/20 1/20 2/20 | No phage isolated | 0/20 0/20 0/20    0/20 0/20 0/20 |
| NSI1303 | SWI002 | BE sewage waterway (outside) | 12/20 11/20 13/20 | No phage isolated | 9/20 1/20 7/20 |
| NSI1330 | SWI002 | BE sewage waterway (outside) | 4/20 2/20 3/20 | No phage isolated | 1/20 1/20 1/20 |
| NSI1479 | SWI002 | BE sewage waterway (outside) | 7/20 2/20 4/20 | No phage isolated | No phage isolated |
| NSI1485 | SWI002 | BE sewage waterway (outside) | 13/20 10/20 13/20 | No phage isolated | 0/20 0/20 0/20 |

PA on plates with FBS grew at RT

FIGURE 8B

*Pseudomonas aeruginosa* (S4)

| Bacterial code | Water source code | Water source name | Phage | | |
|---|---|---|---|---|---|
| | | | Only media | FBS at 37°C+Sh | SB at RT non-Sh |
| NSI1446 | SWI002 | BE sewage waterway (outside) | No phage isolated | 14/20<br>13/20<br>3/20 | No phage isolated |
| NSI1489 | SWI002 | BE sewage waterway (outside) | 8/20<br>8/20<br>4/20 | 15/20  14/20<br>15/20  14/20<br>4/20   3/20 | No phage isolated |
| WIQ0100 | SWI002 | BE sewage waterway (outside) | No phage isolated | No phage isolated | No phage isolated |
| WIQ0200 | SWI002 | BE sewage waterway (outside) | 8/20<br>8/20<br>4/20 | 18/20<br>18/20<br>4/20 | No phage isolated |
| WIQ0240 | SWI002 | BE sewage waterway (outside) | 9/20<br>9/20<br>4/20 | 15/20<br>14/20<br>4/20 | No phage isolated |

PA on plates with SB grew at RT

FIGURE 9A

*Pseudomonas aeruginosa* (S4)

| Bacterial code | Water source code | Water source name | Phage | | |
|---|---|---|---|---|---|
| | | | Only media | FBS at 37ºC+Sh | SB at RT non-Sh |
| NSI1333 | SWI004 | PE sewage waterway | No phage isolated | No phage isolated | No phage isolated |
| NSI1336 | SWI004 | PE sewage waterway | No phage isolated | 13/20 13/20 10/20 | 12/20 12/20 7/20 |
| NSI1405 | SWI004 | PE sewage waterway | 13/20 13/20 10/20 | 13/20 13/20 10/20 | 11/20 12/20 8/20 |
| NSI1446 | SWI004 | PE sewage waterway | 13/20 13/20 10/20 | 13/20 13/20 10/20 | No phage isolated |
| WIQ0100 | SWI004 | PE sewage waterway | 13/20 13/20 9/20 | 13/20 13/20 9/20 | No phage isolated |

*PA on plates with SB grew at RT*

FIGURE 9B

*Acinetobacter baumannii* (S5)

| Bacteria code | Water source code | Water source name | Phage | | |
|---|---|---|---|---|---|
| | | | Only media | FBS at RT non-Sh | SB at RT non-Sh |
| WIQ0134 | SWI004 | PE sewage waterway | 1/20 1/20 1/20 | 1/20 1/20 1/20    1/20 1/20 1/20 | 1/20 1/20 1/20    1/20 1/20 1/20 |
| WIQ0216 | SWI004 | PE sewage waterway | No phage isolated | No phage isolated | No phage isolated |
| WIQ0224 | SWI004 | PE sewage waterway | No phage isolated | No phage isolated | No phage isolated |
| WIQ0230 | SWI004 | PE sewage waterway | No phage isolated | No phage isolated | No phage isolated |
| WIQ0239 | SWI004 | PE sewage waterway | 5/20 2/20 4/20 | No phage isolated | No phage isolated |

AB on plates with FBS and SB grew at RT

FIGURE 10A

*Acinetobacter baumannii* (S5)

| Bacteria code | Water source code | Water source name | Phage | | |
|---|---|---|---|---|---|
| | | | Only media | FBS at RT non-Sh | SB at RT non-Sh |
| WIQ0088B-1 | SWI002 | BE sewage waterway (outside) | 1/20 1/20 1/20 | 1/20 1/20 1/20 / 1/20 1/20 1/20 | 1/20 1/20 1/20 / 1/20 1/20 1/20 |
| WIQ0105 | SWI002 | BE sewage waterway (outside) | 1/20 1/20 1/20 | 1/20 1/20 1/20 / 2/20 1/20 1/20 | 1/20 1/20 1/20 / 1/20 1/20 1/20 |
| WIQ0216 | SWI002 | BE sewage waterway (outside) | 1/20 1/20 1/20 | 1/20 1/20 1/20 | 1/20 1/20 1/20 |
| WIQ0224 | SWI002 | BE sewage waterway (outside) | No phage isolated | No phage isolated | No phage isolated |
| WIQ0230 | SWI002 | BE sewage waterway (outside) | No phage isolated | No phage isolated | No phage isolated |

*AB on plates with FBS and SB grew at RT*

FIGURE 10B

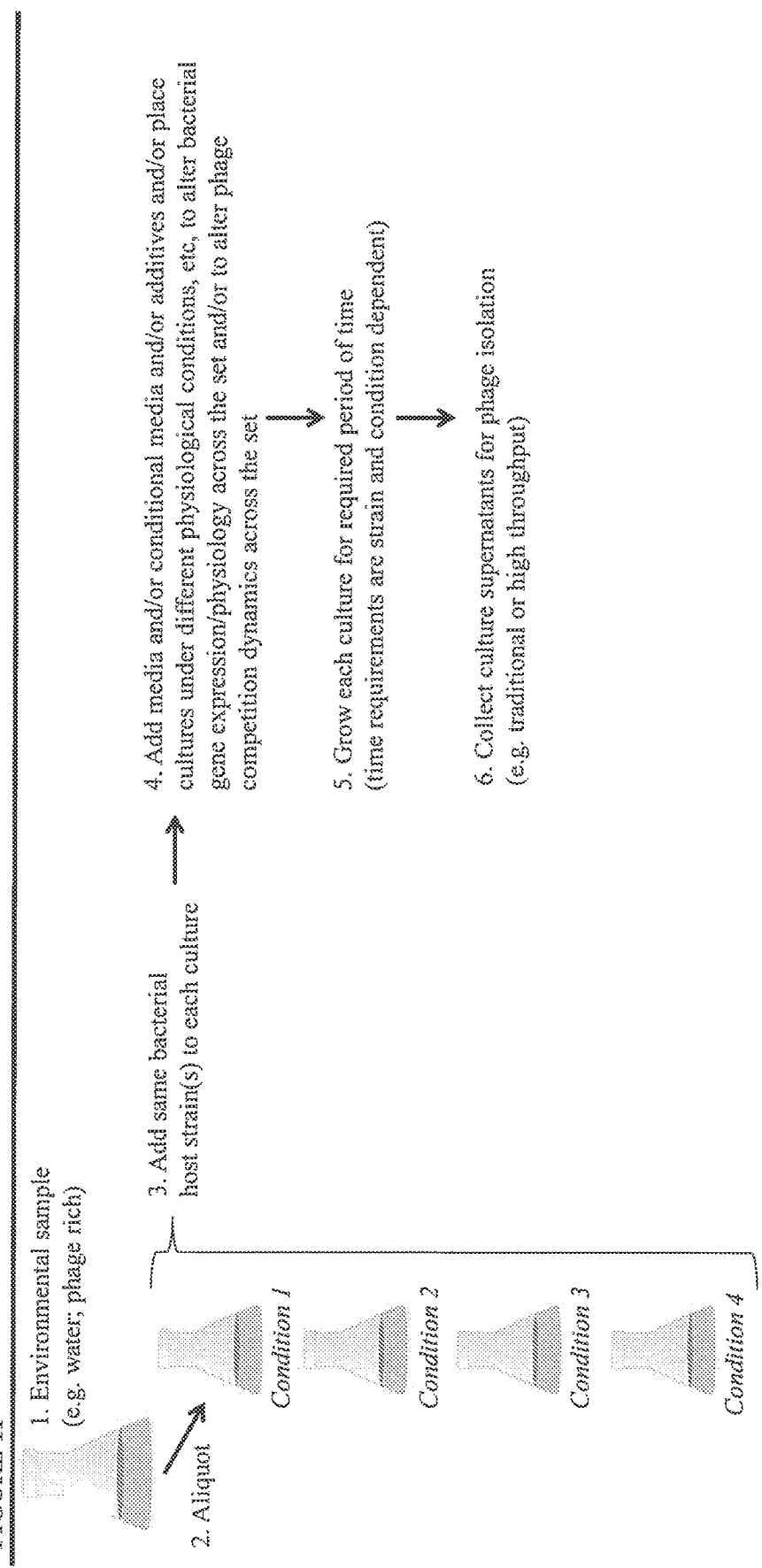

METHODS OF IDENTIFYING BACTERIOPHAGES THAT CAN INFECT AND KILL HOST-ADAPTED INFECTIOUS PATHOGENIC BACTERIA

CROSS REFERENCE TO RELATED APPLICATIONS

The present application claims the benefit of U.S. Provisional Patent Application No. 62/550,461 filed Aug. 25, 2017, the entire contents of which are incorporated by reference herein.

FIELD OF THE INVENTION

The subject matter of the instant invention relates to methods of enhancing harvesting of bacteriophages ("phages") against a targeted host bacteria from a sample comprising phages. Particularly, the methods of the invention are directed to increasing phage harvesting efficiency as well as enhancing the yield and diversity of phages isolated from environmental samples. The focus of the invention also includes improved methods of isolating phages having an enhanced propensity for infecting and killing bacterial pathogens in vivo, including host-adapted infectious pathogenic bacteria. It is contemplated herein that the methods of the instant invention may be used to create robust collections of phages ("phage libraries") comprising phages with greater diversity against bacterial strains, including multidrug resistant (MDR) bacterial pathogens, than phage libraries prepared according to conventional methods. It is also contemplated herein that the methods and compositions of the instant invention will facilitate not only the design of phage therapeutics with superior clinical efficacy, but also provide phage-based diagnostic methods as well as methods of bacterial detection for industrial applications which provide superior performance.

BACKGROUND OF INVENTION

MDR bacterial infections are an increasing problem for military and civilian populations alike. Military populations are at an especially increased risk for resistant bacterial infections as traumatic injuries sustained during combat and military service are highly susceptible to infection, and often require prolonged hospitalization, further increasing the risk of drug-resistant nosocomial infections. For example, MDR ESKAPE pathogens (*Enterococcus faecium, Staphylococcus aureus, Klebsiella pneumoniae, Acinetobacter baumannii, Pseudomonas aeruginosa*, and *Enterobacter* spp.) are known to cause a significant number of the infectious complications in wounded service members, and these organisms greatly increase morbidity and mortality. Treatment options for these kinds of resistant infections are extremely limited and there is a paucity of new drugs in the pharmaceutical pipeline.

In recent years, phage therapy has re-emerged as a potential alternative treatment for MDR bacterial infections. Lytic phages (bacterial viruses) are extremely abundant obligate intracellular parasites that infect, replicate within, and kill very specific bacterial hosts, phage therapy has typically involved using combinations of different lytic phages deemed likely to target and kill a specific bacterial pathogen. Recently, advances in phage therapeutics and antibacterial phage therapy have played a role in several surprisingly highly successful eIND cases in the U.S., and in view of promising advances such as these in the field, there is continued interest in pursuing clinical trials investigating different therapeutic modalities comprising phages.

Notably, phages can be very strain-specific. Thus, in contrast to early efforts in the field of phage therapeutics, and as clearly demonstrated in recent clinical eIND cases, phage therapy may fundamentally require a significant amount of personalization. That said, whether the phage therapeutic comprises population level cocktails, engineered phages, or involves a phage library-to-cocktail personalized therapeutic approach, all of these modalities would benefit greatly from a coordinated and massive expansion of phage libraries against bacterial pathogens, including MDR pathogens such as the ESKAPE pathogens. See, e.g., US 2017/0368116 A1, the entire contents of which are incorporated by reference herein.

In addition to clinical uses in antibacterial pharmaceutical compositions, phage specificity for its target bacterial host may be exploited clinically in methods of diagnosing bacterial infections via a phage-based diagnostic. By culturing clinical samples in the presence of a phage-based diagnostic, the increase in the phage population would indicate the presence of the phage's bacterial host. Thus, by monitoring the phage population, the identification of a specific bacterial pathogen(s) in a clinical sample can be achieved rapidly without the need for bacterial strain isolation. Moreover, phage specificity may also be exploited in methods of detecting bacteria in the environment or in industrial samples, again through the use of a phage-based diagnostic. See, e.g., U.S. Ser. No. 15/994,855 the entire contents of which are incorporated by reference herein. Significantly, since phages require a viable host in which to replicate, phages can discriminate between live bacterial cells and the presence of dead bacterial cells or cell debris, which other molecular detection technologies cannot manage. Thus, in addition to clinical applications in therapeutics and diagnostic methods, phages may also be employed in industrial settings, e.g., where the need to detect live bacterial contamination is a concern.

Phage-based methods of detection and diagnosis take advantage of the ability of a phage to infect and replicate within its bacterial host such that phage titer often increases 10 to even 100-fold in a single generation, constituting a massive increase in a specific "signal." This massive increase in the phage titer "signal" can be exploited for industrial and clinical purposes by monitoring the increase in phage titer using a number of techniques comprising, e.g., classical phage titer counts, quantitative real-time PCR, probes of the phage genome or other reporter constructs, nucleic acid hybridization or other molecular assays, fluorescence or immunofluorescence assays with labeled phage particles, etc.

While phage-based diagnostics and methods of detection represent a powerful tool, such methodologies are also constrained by the same lack of robust collections of phages which currently restricts the development of phage therapeutics. Indeed, phage specificity for its bacterial host is both a strength and a weakness of phage therapeutics; a major hindrance to the continued advancement of all available phage therapeutic modalities is the current lack of sufficiently diverse phage libraries which demonstrate promise for clinical and/or industrial use. Specifically, robust phage libraries against MDR bacterial pathogens, and especially against each of the ESKAPE pathogens, are urgently needed.

Establishing a diverse and robust phage library for clinical and/or industrial uses first requires the isolation of appropriate, relevant phages from the staggering number of phages in the wild. Traditionally, classical phage harvesting first involves mixing raw environmental water samples (rich in diverse phages) with culture media (often in powder form) and a high titer of bacteria against which phages are desired. Ideally, several different bacterial strains are provided with the culture media simultaneously (e.g., from 1-10 bacterial strains in some cases), and these added bacterial strains facilitate the expansion of any phage populations against said bacteria present in the sample. Typically, this mixed culture is then grown overnight at 37° C. with shaking (aerobically) to allow for phage expansion and the enrichment of phages against the said targeted bacteria. The phage-rich supernatant of this culture is then subjected to classical plaquing assays to identify whether phages against the targeted bacterial strain(s) are present in this expanded and mixed phage population. If such phages are present, they are isolated and purified. This general method is currently used for phage harvesting and library construction for both therapeutics and diagnostics.

Notwithstanding the usefulness of current conventional methods, the fact remains that classical phage harvesting methodologies have several limitations. For example, using currently available harvesting methods, any phages against the targeted bacterial strains in the mixed phage population of a phage harvesting culture will emerge based on an in vitro competition among all the phages present in the environmental sample. As such, it is contemplated herein that the "winners and losers" of this interphage competition may reflect, and depend upon, the culture conditions employed. As a result, there may be valuable phages present in a conventional harvesting culture that might have industrial and/or clinical uses against the targeted bacterial strains, but which get relentlessly out-competed in the milieu of classical in vitro harvesting culture conditions. Thus, it is contemplated herein that phage libraries built using only classical in vitro cultures and growth conditions cannot fully exploit the vast extent of phage diversity present in the wild.

While clearly indispensable to biomedical research, one of skill in the art appreciates the inherent limitations of in vitro cultures; while extremely useful, data provided from such cultures may not truly reflect the complexity of in vivo conditions. Thus, it is further contemplated herein that conventional harvesting cultures may enrich for phages from the wild that are specific to the targeted host bacteria when grown in the in vitro physiological conditions of the microbiological culture media, but not specific to the same target bacteria under in vivo conditions, i.e., when in the form of a "host-adapted bacteria" growing in a human or animal host. Thus, phage libraries for in vivo therapeutic and diagnostic use built using classical methods may be unfortunately skewed by comprising phages with limited usefulness for in vivo applications. Thus, taken together with interphage competition, phages which demonstrate in vitro specificity for a targeted bacterial strain not only may prove to have limited clinical use against said bacteria present under the physiological conditions of the human or animal host, but also such phages in in vitro harvesting cultures may actually be out-competing other phages in the culture that might be better able to infect the same target bacteria when host-adapted in vivo.

In view of the foregoing, there remains a need not only for improved methods of enhancing the isolation of different phages from the wild, e.g., from environmental samples, but also for improved methods for identifying phages which can infect and kill targeted bacterial pathogens, and especially host-adapted infectious pathogenic bacteria in vivo. Such improved methods would facilitate the creation of robust phage libraries of enhanced diversity for use in all types of industrial and clinical applications, including but not limited to clinical modalities comprising the use of personalized phage therapeutics with improved clinical efficacy, as well as for improved methods of detecting and/or diagnosing bacteria in both clinical and non-clinical settings via phage-based diagnostics.

SUMMARY OF THE INVENTION

In a first aspect, the invention relates to a method of enhancing harvesting of phages against a targeted host bacteria from a sample comprising phages, said method comprising culturing aliquots of said sample in a plurality of cultures comprising said targeted host bacteria, wherein said plurality of cultures comprises different culture conditions, wherein each of said culture conditions is designed to support growth of said bacteria and produce physiological differences in said bacteria in said plurality of cultures to promote different phage competition outcomes in said plurality of cultures.

In another aspect, the invention relates to a method of identifying phages likely to have an enhanced propensity to infect and kill an infectious pathogenic bacteria in vivo, said method comprising:

a. culturing the infectious pathogenic bacteria in one or more cultures in vitro, wherein said one or more cultures comprises culture conditions comprising one or more culture features and/or additives designed to produce a physiological state and/or gene expression pattern in said infectious pathogenic bacteria in vitro that is more similar to that of said infectious pathogenic bacteria when host-adapted in vivo;

b. culturing a sample comprising phages in said one or more cultures; and c. assaying said one or more cultures to identify phages in the sample that can infect and kill the infectious pathogenic bacteria in vitro under said culture conditions, wherein said identified phages are likely to have an enhanced propensity to infect and kill the infectious pathogenic bacteria in vivo.

In one embodiment of the above aspects, the culture conditions produce one or more changes in the bacteria that occurs in vivo during host-adaptation. In one embodiment of the above aspects, the culture conditions produce one or more changes in gene expression in the bacteria. In a particular embodiment of the above aspects, said changes in gene expression comprises changes in genes expressing bacterial surface features used as phage receptors.

In various embodiments, the methods of the invention are used to harvest and/or identify phages from any possible source. In particular embodiments of the above aspects, the sample comprising phages comprises one or more wild phages. In another embodiment, the sample comprising phages comprises one or more previously isolated phages. In a particular embodiment, the previously isolated phage is obtained from academic, commercial, or noncommercial sources.

In a particular embodiment, the sample comprising phages is collected from one or more natural or man-made sources. In particular embodiments, the source is selected from the group consisting of soil, water treatment plants, raw sewage, sea water, lakes, rivers, streams, standing cesspools, animal intestines, human intestines, manure or other fecal matter, organic substrates, biofilms, and medical/hospital sources.

In another embodiment, the culture conditions comprise variations in one or more culture features or additives selected from the group consisting of culture temperature, culture time, osmotic pressure, pH, $CO_2$ percentage, $O_2$ percentage, nutrient concentration(s), carbon source(s), carbon source concentration(s), growth factor concentration(s), hormone concentration(s), in vitro culture surface characteristics, and concentration of inducer(s) of bacterial virulence factors. In a particular embodiment, the nutrients are selected from the group consisting of amino acids, carbohydrates, vitamins, and minerals. In a particular embodiment, the variations in culture feature or additives are selected from the group consisting of iron concentration, magnesium concentration, concentration of whole or fractions of mammalian serum, concentration of whole or fractions of mammalian plasma, concentration of mammalian blood, and concentration of mammalian tissue homogenates, including homogenates of organs, muscle, and bone. In a particular embodiment, the mammalian serum is fetal bovine serum (FBS). In a particular embodiment, the additive is sheep blood. In a particular embodiment, the additive may or may not be a heat-inactivated substance.

In a particular embodiment, the culture conditions and/or the culture surface characteristics support the growth of the targeted host bacteria in a biofilm. In a particular embodiment, said culture surface comprises materials selected from the group consisting of plastics, metals, surfaces coated with complex host extracts, tissue lysates, biological homogenates, cells, cells debris, and bone.

In one embodiment, the culture surface comprises materials selected from the group consisting of biotic and abiotic surfaces. In a particular embodiment the biotic surface comprises materials selected from the group consisting of collagen, bone, tissue explants, tissue lysates, homogenized tissue material, human or mammalian cells, and cell debris. In another particular embodiment, the abiotic surface comprises materials selected from the group consisting of metals and plastic. In a particular embodiment, the metals are selected from the group consisting of stainless steel, titanium, and aluminum.

In a particular embodiment, the culture temperature is less than about 37° C. In another embodiment, the culture temperature is greater than about 37° C. In yet another embodiment, the culture temperature is about 10° C. to about 42° C. In another embodiment, the culture temperature is about 20° C. to about 25° C. ("room temperature").

In another particular embodiment, the iron concentration is about 0 µM to less than about 0.3 µM. In another embodiment the iron concentration is less than about 2 µM. In a particular embodiment, the iron provided is selected from the group consisting of chelated-iron, nitrate salts, and sulfate salts. In a particular embodiment, the iron concentration is a limiting iron concentration.

In yet another particular embodiment, the serum concentration is about 0-15%. In a particular embodiment, the serum concentration is about 7.5%. In another embodiment, the serum is selected from the group consisting of human serum, animal serum, and a combination thereof. In a particular embodiment, the animal serum is fetal bovine serum (FBS). In a particular embodiment, the serum is provided as whole serum. In a particular embodiment, the serum may be fractionated by heat, centrifugation, or fractioned biochemically using column chromatography prior to addition to the cultures. In a particular embodiment, the serum may or may not be heat inactivated. In a particular embodiment, the cultures comprise 7.5% FBS.

In yet another particular embodiment, the plasma concentration is about 0-15%. In a particular embodiment, the plasma concentration is about 7.5%. In another embodiment, the plasma is selected from the group consisting of human plasma, animal plasma, and a combination thereof. In a particular embodiment, the plasma is provided as whole plasma. In a particular embodiment, the plasma may be fractionated by heat, centrifugation, or biochemically using column chromatography prior to addition to the cultures. In a particular embodiment, the plasma may or may not be heat inactivated.

In yet another particular embodiment, the whole blood concentration is about 0-15%. In yet another particular embodiment, the whole blood concentration is about 5%. In a particular embodiment, the whole blood is selected from the group consisting of human blood, animal blood, and a combination thereof. In a particular embodiment, the animal blood is sheep blood. In a particular embodiment, the cultures comprise 5% sheep blood.

In another embodiment, the concentration of inducer(s) of bacterial virulence factors is about 0-15%. In a particular embodiment, the inducer(s) of bacterial virulence factors is selected from the group consisting of charcoal, glucose-6-phosphate, cholesterol, and fetal bovine serum (FBS). In a particular embodiment, the concentration of glucose-6-phosphate or cholesterol is about 2 g/L and about 100 mg/L, respectively.

In a particular embodiment, the nutrient concentration is limited by using minimal media in the cultures for bacterial growth. In another embodiment, the pH is from about pH 6.5 to about pH 8.5.

In yet another embodiment, the $CO_2$ percentage is about 0-7% $CO_2$. In a particular embodiment, the $CO_2$ percentage is about 5% $CO_2$.

In yet another embodiment, the $O_2$ percentage in about 0-20% $O_2$. In a particular embodiment, the $O_2$ percentage is less than about 2% $O_2$.

In another embodiment, the cultures may be grown for less than about 18 hours. In another embodiment, the cultures are grown about 8 hours. In another embodiment, the cultures are grown overnight. In another embodiment, the cultures may be gown for about 18-36 hours or more.

In another embodiment, the cultures are grown aerobically or non-aerobically (with or without shaking the cultures), or a combination of both. In a particular embodiment, the cultures are grown with shaking at 250 rpm.

In another aspect, the invention relates to a composition comprising one or more phages identified according to the methods of the instant invention. In a particular embodiment, the composition is a pharmaceutical composition. In another embodiment, the composition is for use with diagnostic methods or methods of detecting bacteria.

In yet another aspect, the invention relates to a phage library comprising one or more phages identified according to the methods of the instant invention. In one embodiment, the phage library is against a MDR bacterial pathogen. In a particular embodiment, the phage library is against an MDR ESKAPE bacterial pathogen selected from the group consisting of *Enterococcus faecium, Staphylococcus aureus, Klebsiella pneumoniae, Acinetobacter baumannii, Pseudomonas aeruginosa*, and *Enterobacter* spp.

In yet another aspect, the invention relates to a method of treating a bacterial infection in a subject in need thereof comprising administering to the subject an effective amount of a pharmaceutical composition comprising one or more phages identified according to the methods of the instant invention. In a particular embodiment, the bacterial infection to be treated is selected from the group consisting of wound infections, surgical hardware associated infections, post-surgical infections, and systemic bacteremia.

In additional aspects, the invention relates to methods of diagnosing or detecting bacteria in clinical and non-clinical settings comprising employing phages harvested according to the methods of the instant invention and/or derivatives thereof, e.g., engineered phages. In particular embodiments, the methods of the instant invention are used to diagnose or detect bacteria in biotic and/or abiotic samples. In a particular embodiment, the biotic sample is a sample from an infected mammalian host. In a particular embodiment, the biotic sample is selected from the group consisting of blood samples, sputum samples, swabs from mucus membranes or wounds, biopsies, and puss. In a particular embodiment, the abiotic sample is selected from the group consisting of industrial samples, food samples, pharmaceuticals, makeup and beauty products, and swabs from machinery.

In a particular embodiment, the invention relates to methods of detecting or diagnosing the presence of a targeted bacteria, said method comprising harvesting phages according to the methods of the instant invention, and employing one or more of said harvested phages in assays to diagnose or detect said targeted bacteria. In a particular embodiment, said assays comprise detecting levels of phage infection and/or phage titer levels, wherein evidence of phage infection and/or an increase in phage titer levels indicate presence of the targeted bacteria. In particular embodiments, the phage titer levels are assayed using methods selected from the group consisting of plaquing assays, PCR, nucleic acid hybridization, labeling, and immunolabeling. In a particular embodiment, the PCR method is real-time PCR.

BRIEF DESCRIPTION OF THE DRAWINGS

FIG. 5 depicts data collected from *K. pneumoniae* (KP) phages harvested via traditional and conditional cultures. Each row is specific for a *K. pneumoniae* host strain, and each phage image (hexagon) represents an isolated phage under each condition (column). Per row, the color/shading of the phage represents host range, with the same color indicating the phages had identical host-ranges among the complete set of 20 *K. pneumoniae* strains tested. The number inside of the phage figure (hexagon) is the number of strains that each phage infects, including its host. The "+" means the yield of phages was significantly increased in that condition.

FIG. 6, FIG. 7, FIG. 8A, FIG. 8B, FIG. 9A, FIG. 9B, FIG. 10A, and FIG. 10B depict data for studies described in Example 2. FBS, 7.5% fetal bovine serum; SB, 5% sheep blood; RT, room temperature; Sh, with shaking (250 rpm); non-SH, without shaking. Each type of hexagon (solid, dashed, dotted, colored) represents a different phage that was isolated against the host strain in question (row) and under the condition in question (column), as defined by host range against a set of 20 different host strains of the same species in question (*K. pneumoniae* in FIGS. 6-7, *P. aeruginosa* in FIGS. 8A, 8B, 9A and 9B, and *A. baumannii* in FIGS. 10A and 10B.) The three ratios of numbers in the hexagon indicate the following: The top ratio refers to the number of strains that the phage infected over 20 strains on plates with only tryptic soy broth (TSB); the middle ratio refers to the number of strains that the phage infected over 20 strains on plates in TSB with FBS added; the bottom ratio refers to the number of strains that the phage infected over 20 strains on plates in TSB with SB added. Each row is independent, the same outline pattern/color in each row means that the phage infected the same strains under the same conditions. Different color in each row means that the phages infected different strains and/or under different conditions.

FIG. 6 depicts phages that were isolated against the listed 5 MDR strains of *K. pneumoniae* (KP) using the strategy of the instant invention in which a single environmental sample was aliquoted across a set of three harvesting cultures containing: the listed KP strains, the aliquoted water, TSB, or TSB+7.5% FBS, or TSB+5% SB.

FIG. 7 depicts phages that were isolated against the listed 5 MDR strains of *K. pneumoniae* (KP) using the strategy of the instant invention in which a single environmental sample was aliquoted across a set of three harvesting cultures containing: the listed KP strains, the aliquoted water, TSB, or TSB+7.5% FBS, or TSB+5% SB.

FIG. 8A depicts phages that were isolated against the listed 5 MDR strains of *P. aeruginosa* (PA) using the strategy of the instant invention in which a single environmental sample was aliquoted across a set of three harvesting cultures containing: the listed PA strains, the aliquoted water, TSB, or TSB+7.5% FBS, or TSB+5% SB.

FIG. 8B depicts phages that were isolated against the listed 5 MDR strains of *P. aeruginosa* (P) using the strategy of the instant invention in which a single environmental sample was aliquoted across a set of three harvesting cultures containing: the listed PA strains, the aliquoted water, TSB, or TSB+7.5% FBS, or TSB+5% SB. 0/20 ratio for NSI0978 and NSI1485 indicates phages isolated with SB did not grow in any of the 20 strains tested including their host original strain.

FIG. 9A depicts phages that were isolated against the listed 5 MDR strains of *P. aeruginosa* (PA) using the strategy of the instant invention in which a single environmental sample was aliquoted across a set of three harvesting cultures containing: the listed PA strains, the aliquoted water, TSB, or TSB+7.5% FBS, or TSB+5% SB.

FIG. 9B depicts phages that were isolated against the listed 5 MDR strains of *P. aeruginosa* (PA) using the strategy of the instant invention in which a single environmental sample was aliquoted across a set of three harvesting cultures containing: the listed PA strains, the aliquoted water, TSB, or TSB+7.5% PBS, or TSB+5% SB.

FIG. 10A depicts phages that were isolated against the listed 5 MDR strains of *A. baumannii* (AB) using the strategy of the instant invention in which a single environmental sample was aliquoted across a set of three harvesting cultures containing: the listed PA strains, the aliquoted water, TSB, or TSB+7.5% FBS, or TSB+5% SB.

FIG. 10B depicts phages that were isolated against the listed 5 MDR strains of *A. baumannii* (AB) using the strategy of the instant invention in which a single environmental sample was aliquoted across a set of three harvesting cultures containing: the listed PA strains, the aliquoted water, TSB, or TSB+7.5% PBS, or TSB+5% SB.

FIG. 11 depicts a possible strategy disclosed herein for a method of enhancing harvesting of phages against a targeted host bacteria from a sample comprising phages. The sample can be from any source. As depicted therein, Steps 1-5 depict creating different cultures comprising different aliquots of the same environmental water sample cultured in the presence of the same bacterial host strain under different culture conditions. As depicted therein, step 6 comprises collecting phage supernatants for phage isolation, e.g., using conventional methods or high throughput. Each culture supernatant obtained in step 6 may contain differentially enriched subsets of the available phages in the original environmental sample (1). Without being bound by any particular theory, it is contemplated herein that these phages may use different receptors and/or show differing abilities to infect conditionally adapted bacterial cells (including host-adapted cells) and/or show conditional dependence for infection and/or show different tolerances to changing conditions and/or have different intrinsic characteristics. Thus the methods of the instant invention can be used to identify phages that may be better (or worse) for use in therapeutics or diagnostics.

DETAILED DESCRIPTION

Figure 1:
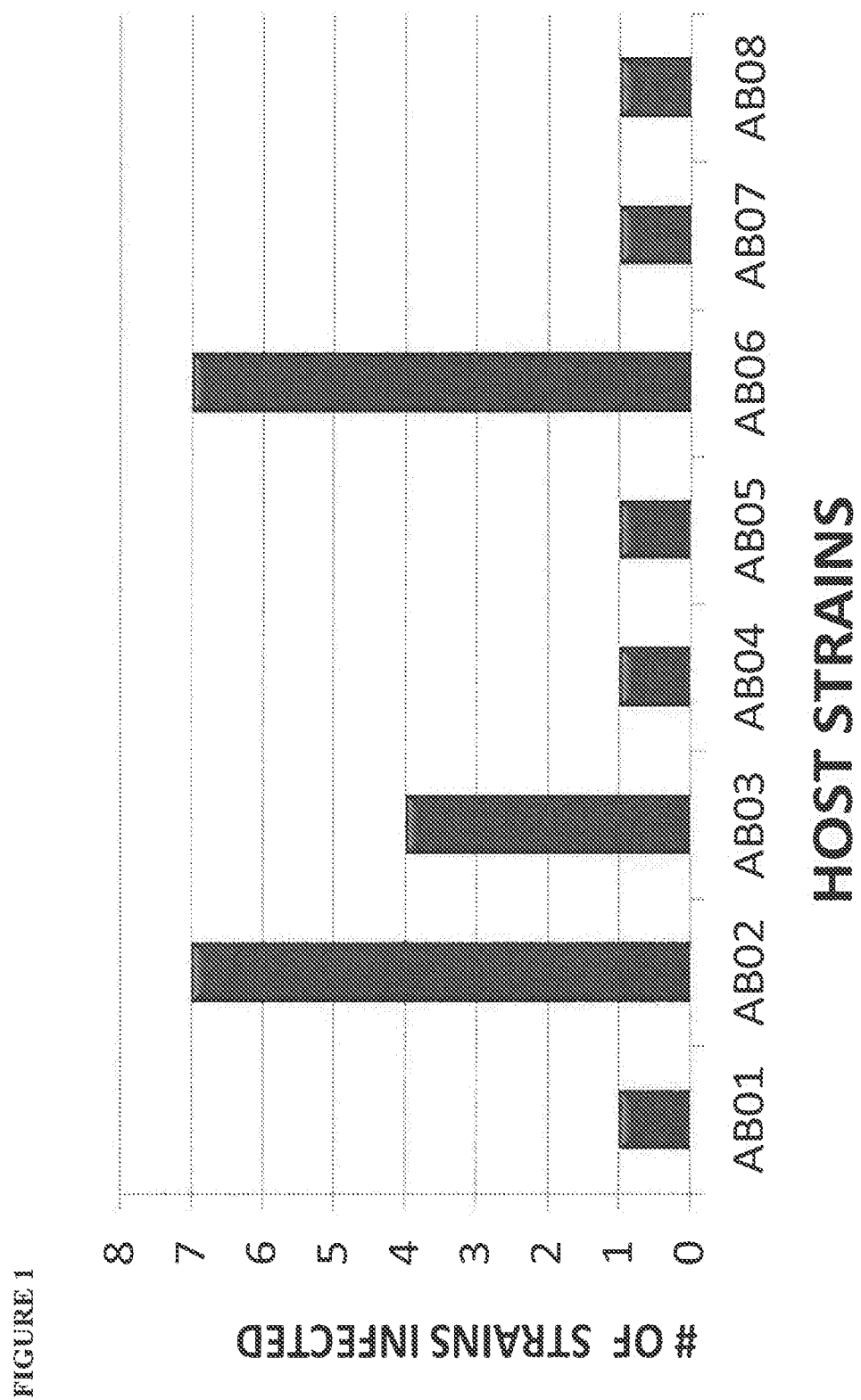
FIG. 1 depicts host ranges of various *A. baumannii* (AB) phages isolated from the Peruvian Amazon in 2017. The magnitude of the bar is the total number of AB strains tested that each phage can infect.

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made are at 25° C. and normal pressure unless otherwise designated.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include components in addition to those recited in the claim, but only if the additional components do not materially alter the basic and novel characteristics of the claimed invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a phage" can mean at least one phage, as well as a plurality of phages, i.e., more than one phage.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

Lytic phages typically infect bacteria by docking to receptors on the bacterial surface, injecting their genetic material (usually DNA), producing their progeny within the bacterial cell using bacterial machinery, and finally lysing the bacterial cell upon progeny release, killing the bacterial cell in the process. All of these steps are necessary in order for a phage to successfully replicate and kill an infected bacterial cell, and all of these steps are absolutely dependent on the physiological state and health of said bacterial cell.

The mechanisms of action regarding phage infectivity and replication within its target bacterial host poses a challenge in the design of phage-based therapeutics as well as phage-based methods of diagnosing or detecting bacteria. As discussed above, it is well known that in vitro cultures cannot completely duplicate in vivo conditions. This is true for bacterial cultures, including cultures of human pathogens such as the ESKAPE pathogens. Thus, a pathogenic bacterium growing outside of a host very likely does not express the same proteome as that expressed by said bacterium when infecting a host, i.e., when the bacterium's gene expression is "host-adapted." Thus, notably, during phage isolation in vitro, the targeted bacterial pathogen typically adapts its physiology, gene expression, and therefore its surface receptor repertoire, in response to the particular culture conditions used during phage isolation; i.e., typically, standard growth media grown aerobically at 37° C. Accordingly, during phage isolation procedures, all of the phage replication steps that take place within the bacterial cell in vitro reflect, and thus are naturally limited by, the parameters of bacterial gene expression set by the in vitro culture conditions.

Thus, it is contemplated herein that since standard classical culture techniques using standard growth media and temperature may restrict the gene expression pattern of a bacterium and may result in a receptor repertoire or physiological state that is unique and/or significantly different from that of the same bacterium growing in a host in vivo, current in vitro methods of isolating phages for possible clinical and industrial use may fail to maximize the isolation of available phages in an environmental sample, and thus may fail to identify all potentially useful phages in the sample. Moreover, conventional phage harvesting methods may in fact actually enrich for phages optimally suited to infecting and killing bacteria grown in conventional culture conditions, but not bacteria growing in and causing an infection in a host organism. As discussed above, bacteria grown under specific culture conditions may not express surface receptors that are expressed in other conditions or in vivo, and similarly bacteria in vitro may express surface receptors that are not expressed at all in vivo. Without being bound to any particular theory, it is contemplated herein that such receptors may act as "decoys" in conventional methods of phage harvesting by selecting for phages that can infect and kill a bacterial strain in vitro, and/or only under certain specific or narrow conditions in vitro, but which will actually have little therapeutic efficacy on the same bacterial strain in vivo. Thus, phages isolated on bacteria raised in conventional cultures may be suboptimal or even incapable of infecting pathogenic bacteria during a bona-fide infection in a human or animal.

Accordingly, it is contemplated herein that there remains a need not only for improved methods of harvesting wild phages from both man-made and natural sources, but also for identifying phages which can specifically infect and kill bacterial pathogens in vivo, especially host-adapted infectious pathogenic bacteria, and particularly, MDR bacteria. Improved methods for harvesting and identifying such phages will enable the creation of robust diverse phage libraries which in turn can be used to create various types of phage-based therapeutics and diagnostics for clinical applications. In a particular embodiment, it is contemplated herein that the methods of the instant invention can be used to develop diverse phage libraries for compounding personalized phage therapeutics with improved clinical efficacy.

Similarly, as discussed above, one of skill in the art will appreciate that phage diagnostics, though powerful, are limited by the same constraints as phage therapeutics; detecting bacterial hosts in biotic or infected host-derived samples may also be effected by the same gene expression changes in vitro as those effecting phage therapeutics. Similar concerns limit the development and use of phage-based methods of detecting bacteria in industrial applications. Accordingly, isolating phages in vitro using classical conditions, and not accounting for conditional gene expression changes in the targeted bacterial host, may produce phage-based diagnostics and methods of detecting bacteria of limited value in actual application. Instead, effective phage-based diagnostics and phage-based detection methods must consider conditional changes in bacterial gene expression in order to ensure the fidelity of phage-based products and methods. Varying the conditions under which phages are harvested for such uses may allow for the creation of diagnostics and methods of detection that can function under multiple bacterial physiological and gene expression states, including those states in vivo.

It is theorized herein that in a mixed bacterial culture with a mixed phage population such as that found in a classical phage harvesting culture, there exists competition between and among phages for access to mutual host bacteria. Thus, it is contemplated herein that exploiting this interphage competition in a harvesting culture, and noting the marked differences that can occur between the gene expression patterns of pathogenic bacteria growing inside and outside a host, offers an intriguing means of optimizing harvesting conditions to favor the isolation of phages against targeted host-adapted bacteria, by inducing a host-adapted like state in vitro in phage harvesting cultures. Additionally, simply varying specific culture conditions across a set of otherwise identical phage harvesting cultures, may produce relative bacterial gene expression differences across the set of cultures and/or modulate interphage competition outcomes, increasing the diversity of phages harvested across that set.

Accordingly, the methods of the instant invention are directed to varying discrete conditional parameters across a set of otherwise identical in vitro phage harvesting cultures, thereby modifying the outcome of phage competition across the set, e.g. the identity of the winning phages (those that increase in titer) and losing phages (those that fail to produce a detectable increase in titer), and therefore increasing the diversity of phages which are eventually isolated from said cultures, e.g., by altering the physiological state and/or concomitant gene expression of the bacterial host(s) in each culture. In a particular embodiment, it is contemplated herein that aliquoting a single sample comprising phages into a set (plurality) of cultures comprising the same bacterial target(s) but comprising differing varying physiological conditions, including culture conditions designed to more closely mirror growth conditions in the host during a bacterial infection in vivo, will increase phage isolation diversity and efficiency across the set and allow for the isolation of phages that can more reliably infect bacteria growing with a "host-adapted" gene expression pattern and surface-feature repertoire than phages isolated according to conventional methods. As a result, the methods of the instant invention will allow different phages to win the competition under those different conditions, thereby increasing the number and diversity of phages isolated from a single sample, thus enabling the creation of more expansive and diverse phage libraries.

Thus, it is contemplated herein that the effective development of numerous phage-based therapeutic modalities, including therapeutics comprising natural phage products, phages engineered to carry antimicrobial cargo, or that possess expanded host-range, phage-based diagnostics, and methods of detecting bacterial contamination, would all benefit from the use of phages that are isolated from diverse culture conditions that can enhance, and even maximize, the isolation of phages from experimental samples.

Accordingly, in a first aspect, the invention relates to a method of enhancing harvesting of phages against a targeted host bacteria from a sample comprising phages, said method comprising culturing aliquots of said sample in a plurality of cultures comprising said targeted host bacteria, wherein said plurality of cultures comprises different culture conditions, wherein each of said culture conditions is designed to support growth of said bacteria and produce physiological differences in said bacteria in said plurality of cultures to promote different phage competition outcomes in said plurality of cultures.

In another aspect, the invention relates to a method of identifying phages likely to have an enhanced propensity to infect and kill an infectious pathogenic bacteria in vivo, said method comprising:

a. culturing the infectious pathogenic bacteria in one or more cultures in vitro, wherein said one or more cultures comprises culture conditions comprising one or more culture features and/or additives designed to produce a physiological state and/or gene expression pattern in said infectious pathogenic bacteria in vitro that is more similar to that of said infectious pathogenic bacteria when host-adapted in vivo;

b. culturing a sample comprising phages in said one or more cultures; and c. assaying said one or more cultures to identify phages in the sample that can infect and kill the infectious pathogenic bacteria in vitro under said culture conditions, wherein said identified phages are likely to have an enhanced propensity to infect and kill the infectious pathogenic bacteria in vivo.

As understood herein, a "targeted host bacteria", "target bacteria" and like terms refers to the bacteria against which one or more phages are sought. These can include, e.g., infectious, pathogenic bacteria. Infectious, pathogenic bacteria are familiar to one of skill in the art and include, but are not limited to, the MDR bacteria discussed in detail herein.

While it is contemplated herein that varying amounts of a sample comprising phages may be used in the methods of the instant invention, in a particular embodiment, sample aliquots of the same volume are used in the methods of the instant invention. In a particular embodiment, constant and discrete amounts of a fluidic and/or solubilized homogenous sample comprising phages are added across a plurality or set of liquid cultures of uniform volume all comprising the same one or more bacterial strains, including target bacterial strains. In a particular embodiment, solid sources of phages (e.g. soil, feces, etc.) are first solubilized in water or other liquid to facilitate aliquoting.

As described herein, the methods of the instant invention allow for the increase in phage isolation from a single sample by aliquoting said sample across a set of phage harvesting cultures, and varying specific culture conditions across the set of otherwise identical cultures. Without intending to be limited to any particular theory or mechanism of action, it is contemplated herein that the methods disclosed herein produce relative bacterial gene expression differences, and/or bacterial physiology differences, and/or modulate interphage competition outcomes across the set of cultures, increasing the diversity of phages harvested across that set from the single sample (see, e.g., FIG. 11 which provides a sample schematic of this concept.) Varying the culture conditions so as to mimic the host environment, and/or to modulate bacterial gene expression and/or physiology so as to recapitulate a "host-adapted" state in the targeted bacteria, may allow for the isolation of phages better able to infect bacterial pathogens in vivo, and/or select against phages that infect in vitro adapted bacteria.

The ability of the methods disclosed herein to produced enhanced phage harvesting results is demonstrated in the results provided in the below examples. For example, FIGS. 6, 7, 8A, 8B, 9A, 9B, 10A and 10B illustrate in numerous bacterial strains and species that the addition of FBS or sheep's blood to harvesting cultures not only diversifies phage harvesting across the set of harvesting cultures, but also that there are phages that are apparently "conditionally isolated" (when scored by host range, arguably the most important feature of a phage with respect to its therapeutic potential). That is, there are phages present in a single sample that can be isolated in the presence of PBS or sheep's blood that cannot be found in media-only traditional cultures, and vice versa. These results illustrate that although these phages are present across the set of cultures via the homogenous aliquoted sample, the conditional cultures produce different "winners" and "losers" from each culture's interphage competition. These experimental cultures and results directly illustrate that it is possible to create culture conditions designed to support growth of bacteria but which also produce physiological difference in the bacteria that can promote different phage competition outcomes in the cultures. To this end, as discussed below in Example 3, future experiments using concentrated mouse organ homogenates that comprise far more complex host materials may improve the ability of conditional culture sets to identify even more phages for clinical and industrial use.

Given the difference in phage harvesting results described herein, employing differences in culture features and additives according to the methods of the instant invention can clearly promote changes in the physiological state of the cultured bacteria and thus enhance phage harvesting. As illustrated in the examples and data provided herein, the method works in multiple different species, however, the exact mechanism as to how these differences in culture features and/or additives change the physiological state of the bacteria, and thus modulate the results of phage competition, is not known.

While the mechanism of action in each bacterial species may vary, the method is nevertheless very robust and likely involves bacterial gene expression differences across the culture set, including, e.g., changes in the expression of bacterial surface proteins that can serve as phage receptors.

Thus, in view of these data, and as discussed below in detail, it is contemplated herein that the invention includes modifying the culture conditions to more closely approach in vivo conditions, thus producing a physiological state and/or gene expression pattern in infectious pathogenic bacteria in vitro that is more similar to that of said infectious pathogenic bacteria when host-adapted in vivo. Accordingly, it is contemplated herein that that such modified culture conditions will be able to identify phages that are more likely to have an enhanced propensity to infect and kill an infectious pathogenic bacteria in vivo.

It is understood herein that varying bacterial culture conditions in vitro according to the methods of the instant invention may not produce bacterial cultures which completely mimic physiological conditions in vivo. Regardless, even if such modified cultures can never fully simulate the host environment, it is contemplated herein that such modifications may nonetheless produce different and distinct physiological and gene expression states in bacteria that may be useful to achieve an enhancement in the isolation of diverse phages from an environmental source compared to conventional methods of phage harvesting. Notably, undue experimentation is not necessary to perform the methods described herein. Indeed, as demonstrated in Example 1 and Example 2 herein, even a modification of a single culture feature or additive (+/−FBS) may be useful to enhance the isolation of phages having different host ranges from a single common water source.

As discussed herein, the methods of the instant invention demonstrate that not only are there phages that show conditionally dependent isolation, but there are phages that show conditionally independent and conditionally dependent infection of the same host. For example, as described in Example 2 and depicted in FIG. 6, harvesting data with bacterial strain WIQ0239 illustrates that a phage was found against this strain in the presence of sheep's blood, and that this phage cannot infect the WIQ0239 host without sheep's blood present. Also, FIG. 6 harvesting data with bacterial strain WIQ0289 illustrates that there was a phage found that was capable of infecting the WIQ0289 host in traditional culture media and under traditional conditions, but cannot infect when either FBS or sheep's blood is added to the culture. These remarkable results indicate that there are phages in the wild that cannot infect their host strain in the presence of biological materials like FBS and sheep's blood, and there are some phages that are incapable of infecting their host strains in the absence of such biological materials. We contemplate herein that it is highly likely these kinds of phages, both conditionally isolated with and conditionally dependent on host biological materials, will show marked differences in their therapeutic utility. Significantly, based on these data, it is contemplated herein that phages which show a preference to infect a bacterial host when in the presence of host biological materials will likely have superior therapeutic potential and an enhanced propensity to kill host-adapted bacteria in vivo.

As understood herein, "enhancing" the harvesting of phages against a target host bacteria includes but is not limited to improving the total yield and/or the efficiency of phage isolation from a sample as compared to conventional methods. It is contemplated herein that "enhancing" the isolation of phages according to the methods of the instant invention comprises the ability to identify a variety of different phages from the same sample, e.g., more diverse phages may be identified from the same sample by altering bacterial culture conditions as described in detail herein.

Significantly, it is contemplated herein that the methods can be used to identify phages having different host ranges.

Similarly, phages with "enhanced propensity" to infect and kill an infectious pathogenic bacteria in vivo identified according to the methods of the instant invention refers to phages that are more likely to infect and kill an infectious pathogenic bacteria in vivo in comparison with phages identified using conventional in vitro methods.

As understood herein, "host-adapted" bacteria are bacteria that have infected an organism, and have undergone a gene expression change or other modification which facilitates the ability of the bacteria to grow in the host organism. One of skill in the art will appreciate that bacterial host adaptation may be characterized using conventional methods without undue experimentation, including but not limited to, analyzing and comparing in vitro and in vivo patterns of gene expression in infectious pathogenic bacteria.

Infectious bacteria frequently grow as a biofilm during an infection. Biofilms are known to have drastically altered cellular surface features and phage receptors relative to cells grown planktonically and/or in traditional cultures. Thus, it is further contemplated herein that the methods of the invention comprise using cultures of bacteria in biofilms to enhance phage isolation and/or identify phages with enhanced propensity to infect and kill infectious pathogenic bacteria in vivo. Accordingly, by varying the physiological conditions of phage isolation cultures and/or mimicking in vivo conditions in vitro with conditional cultures and/or by first growing bacteria as a biofilm and isolating phages against said biofilm, the phages isolated on bacteria grown in these varied cultures according to the methods of the instant invention will maximize diverse phage isolation, for example by enriching for the use of receptors that are specifically expressed during bona-fide infections, thus allowing for better formulation of phage therapeutics and/or diagnostics that more specifically target host-adapted bacterial pathogens or bacteria growing under different conditions.

Conditional Cultures

As one of skill in the art will appreciate, bacteria may be grown, or "cultured" in vitro according to a variety of conventional methods. These conventional cultures include the use of plates and flasks which provide physical surface areas suitable for bacterial growth, incubators which provide proper temperature, humidity, and aerobic or anaerobic conditions, and solid or liquid culture media which provides necessary chemicals and other reagents to support bacterial growth. These media may be modified to include a variety of minerals, nutrients, energy sources, and buffering agents depending on the bacteria being cultured. It is contemplated herein that the methods of the present invention comprise modifying such conventional culture conditions to create various different "conditional cultures", including various different culture conditions, wherein each of said culture conditions is designed to support growth of said bacteria and produce physiological differences in said bacteria in a plurality of cultures to promote different phage competition outcomes in the plurality of cultures. For example, as discussed herein in detail, one or more culture features and/or culture media additives may be varied to produce a myriad of culture conditions for use in the methods of the instant invention.

Specifically, it is contemplated herein that the conditional cultures of the instant invention may be designed to mimic different physiological conditions which occur during bacterial infection in vivo in order to trigger physiological changes in pathogenic bacteria that are likely to mirror the bacterial physiology and gene expression patterns seen during mammalian, e.g., human, infections. In a particular embodiment, it is contemplated herein that changing the physiological conditions of the host bacteria to conditions that better mimic the bacterial physiology and gene expression during an infection will allow for the isolation of phages that use a different repertoire of surface receptors than those available on classical aerobically growing 37° C. cultures. Specifically, it is contemplated herein that in certain embodiments, culture conditions employed in the methods of the instant invention support isolation and identification of phages that recognize a repertoire of surface receptors better-suited to infecting bacteria growing in a human host. Modifying culture conditions and thus altering the gene expression and phage receptor repertoire of the targeted host bacteria will likely enhance and may even maximize the isolation of phages present in an environmental sample, leading to a more diverse phage library from which to build phage-based therapeutics of all modalities and/or phage-based diagnostics.

In a particular embodiment, it is contemplated herein that the use of different culture conditions will trigger different and/or unique but overlapping bacterial gene expression patterns in each condition. Importantly, it is believed that some of the gene expression pattern changes that will occur will be in genes expressing bacterial surface features used as phage receptors. Thus, aliquoting a single sample and culturing the same host strain(s) in a plurality of conditional cultures each containing an aliquot of said sample, will create a set of cultures comprising the same bacteria but expressing different phage receptors across the culture set, allowing each aliquoted conditional culture to select a different subset of the available phages in said environmental source for harvesting, and thus an enhanced variety of different phages may be isolated from a single environmental source.

Similarly, it is also contemplated herein that in a particular embodiment, the culture conditions may be varied to trigger an expression pattern of one or more genes in an infectious pathogenic bacteria in vitro that is similar to an expression pattern of these one or more genes in the infectious pathogenic bacteria during infection of said host in vivo. It is also contemplated herein that some of the induced gene expression pattern changes will be in genes expressing bacterial surface features used as phage receptors.

Specific types of conventional media are familiar to one of skill in the art, and are available from a variety of commercial vendors. These include, for example, simple or basal media, complex media, defined media and special media. In various embodiments, culture media for use in the methods of the instant invention include commercially available "ready to use" microbial culture media. Suitable commercially available microbial culture media that may be used include, e.g., LB, TSB/A, defined rich media, and defined minimal media (discussed below). According to the methods of the instant invention, the microbial culture media may be modified to further comprise various additives and/or to lack certain reagents by design to vary bacterial gene expression and/or induce infection-like gene expression in the bacterial pathogen. Media, reagents, and other additives for use in the methods of the instant invention may be obtained from a wide variety of commercial vendors, e.g., EMD Millipore (Billerica, Mass.); Becton Dickinson (Franklin Lakes, N.J.); Life Technologies (Carlsbad, Calif.); Thermo Fisher Scientific (Pittsburgh, Pa.); and Sigma Aldrich (St. Louis, Mo.)

In addition to using and augmenting or otherwise modifying commercially available, "ready-to-use" liquid or solid culture media for use in the methods of the instant invention, it is also contemplated herein that bacterial culture media may be custom designed using raw materials by one of skill in the art. For example, culture media may be custom formulated for use in the methods of the instant invention starting with a wide variety of commercially available raw materials, base materials, and culture media supplements. Such raw materials are familiar to one of skill in the art and include, e.g., peptones, yeast extracts, as well as defined amino acids, carbon sources, and vitamin components. Similarly, supplements employed for culturing particular bacterial pathogens are familiar to one of skill in the art and include, e.g., defined carbon sources, essential amino acids, and essential micronutrients and vitamins.

It is contemplated herein that one or more culture features may be modified to more closely approximate various physiological aspects associated with a bacterial infection in vivo. However, regardless of how well the media recapitulates in vivo conditions, it is understood herein that varying the bacterial physiological gene expression in phage harvesting and/or isolation cultures according to the methods of the invention will enhance and diversify total phage isolation. Notably, the results provided in the examples provided herein below do not include gene expression data, however, one of skill in the art will appreciate that the varied results, at least in part, likely reflect changes in gene expression. Additionally, the results presented here, which do demonstrate conditionally dependent phage isolation and conditionally dependent phage host-infection, were obtained using numerous bacterial strains and several different bacterial species. The precise mechanism in each species, and possibly in each strain, is likely unique, yet the overall method is robust enough for broad application across numerous strains and species such that the exact mechanism(s) is a nuance.

As discussed in detail below, one or more culture modifications that may be made include but are not limited to: varying the temperature of the cultures (e.g., more or less than 37° C.), modifying (e.g., reducing) the level of iron in the cultures; adding whole or fractionated serum to the cultures; adding whole or fractionated plasma to the cultures; adding organ homogenates such as mouse or other mammalian liver, heart, spleen, and kidney homogenates; modifying the concentration and identity of nutrients in the culture (e.g., nutrient starvation and/or the inclusion of exclusively phosphorylated sugars); modifying the pH of the cultures to stress the bacteria or buffering the culture conditions with a buffer such as carbonic-acid-bicarbonate; modifying the level of magnesium in the cultures (e.g., magnesium limitation); modifying the level of carbon dioxide and/or oxygen (e.g., culturing in anaerobic or microaerophilic conditions) and/or modifying (e.g., increasing) the levels of known inducers of bacterial virulence factors such as activated charcoal, phosphorylated sugars, and/or cholesterol. Gene expression may also be altered to more closely mimic infection pattern by modifying the culture conditions to promote biofilm formation. See e.g., Boyce, J. D., Cullen, P. A., & Adler, B. (2004). Genomic-scale Analysis of Bacterial Gene and Protein Expression in the Host. *Emerging Infectious Diseases*, 10(8), 1357-1362.

Iron Limitation

It has been reported that bacterial gene expression may be modified by reducing iron levels in bacterial cultures. See Paustain et al, infect. Immun 2001 69:4109-4115. Thus, it is contemplated herein that the conditional cultures of the instant invention may be modified to include iron levels in only trace amounts, e.g., well below the range of iron for bacterial growth of 0.3 $\mu M$ to 1.8 $\mu M$. Free iron in the host is nearly non-existent. Iron limiting conditions, and/or iron supplied only in the form a heme, mimics the free-iron concentration and source of iron present during a bona-fide host infection in a human host. For example, in a particular embodiment, one of skill in the art will appreciate that "iron free media" may be created using a defined rich media that eliminates all but trace iron supplied by the trace amounts in the individual components of the defined rich media. Chelators can be added to further reduce the free iron, and/or iron may then be added back in the form of heme to mirror the iron levels and sources of iron present in a mammalian host.

Inducers of Bacterial Virulence Factors

In various embodiments, the methods of the instant invention may comprise mixing raw environmental samples with microbial culture media that is augmented with additives capable of inducing bacterial virulence factors. These factors may or may not also have nutritive value for the bacteria. As understood herein, "bacterial virulence factors" are those gene products of a bacterial pathogen which enable it to invade a host, colonize a host, survive within a host, and/or cause disease within a host. For example, these factors include proteins produced by the bacteria which can facilitate bacterial adhesion to host cells, colonization of the host, invasion of host cells, and/or toxins that directly harm the host. They include fats, carbohydrates, proteins and toxins, found on the surface of the bacteria, in the bacterial cell wall or membrane, or secreted by the bacteria. See, e.g., Wu et al, Current Opinion in Chemical Biology 2008, 12:93-101. Surface features such as these can also serve as phage receptors, and many of these features are not expressed outside of a host or are massively upregulated during the infection of a host. Thus, these factors are often not functionally present in bacteria growing in vitro, and inducing their expression during phage harvesting and/or isolation allows for finding phages that may use them as receptors and therefore may possess enhanced therapeutic efficacy. These additives include but are not limited to: Fetal Bovine Serum (FBS), Glucose-6-Phosphate, activated charcoal, and cholesterol. Modification of culture levels of magnesium have also been reported as affecting the expression of certain virulence factors. See Guina et al, J. Am Soc Mass Spectrom. 2003 14:742-751, the entire contents of which are incorporated by reference herein.

Alterations in bacterial gene expression during the infection of a host may also include the down-regulation of certain genes expressing bacterial surface features. Similarly, the augmented cultures outlined here, intended to produce more host-like physiological states in the bacterial pathogens, may also yield bacteria that specifically "turn off" or downregulate the expression of surface features that are present during traditional in vitro culture growth, but are not present or are downregulated during infection of a host. These now deactivated surface features, when present, may skew or cause the selection of; or favor the isolation of, phages that preferentially infect in vitro adapted bacteria.

Thus, these in vitro associated surface features may serve a decoy function, and their simple absence might enhance the isolation of phages against host-adapted bacteria. This strategy of attempting to turn off receptors and find fewer phages against in vitro adapted bacteria runs completely counter to current methods looking to maximize the identification of so called "broad host range" phages in classical broth cultures in vitro. Thus, it is contemplated herein that, using the methods of the instant invention, one would find less of such bacteria in some conditional cultures across the set of the conditional cultures, with the express purpose of finding phages better-suited to infecting host-adapted bacteria. Specifically, the down-regulation of decoy or specifically in vitro surface features may enhance the isolation of phages that use surface receptors present during both in vitro growth and during an infection, because removing the decoy receptors and therefore the competition of phages that use these receptors normally downregulated during the infection of a host, will enhance the isolation of phages better-suited to infecting host-adapted bacteria. These augmented cultures are then grown at variable temperatures, and under aerobic and anaerobic conditions for the required period of time, e.g. over-night, depending on the strain and condition needs. The phage-rich supernatant of these cultures will be specifically enriched for phages that infect host-adapted bacterial pathogens. These supernatants are then subjected to plaquing assays to identify phages against the target pathogen, if present. For example, methods for analyzing the supernatants include, but are not limited to, traditional plate-based plaquing assays, liquid assays, or high throughput assays. These classical plaquing assays are performed under the same conditions as the augmented cultures so as to maintain the bacterial pathogen in the same physiological state as during the initial isolation. Phages harvested under these conditions can then be screened for therapeutic or diagnostic efficacy.

Serum and Plasma

It is contemplated herein that adding whole or fractionated serum or plasma to bacterial cultures may induce gene expression changes in bacterial pathogens, including changes in virulence factor expression. These changes in gene expression and/or virulence factor expression may include surface proteins or other surface features, and therefore phage receptors. In various embodiments, whole or fractionated serum or plasma for use in the methods of the instant invention are selected from the group consisting of those derived from humans and animals. Serum may be obtained from a variety of commercial vendors, including major distributors such as Fisher and Sigma Aldrich.

Nutrients

Infection of a host presents a bacterial pathogen with in vivo conditions which are nutrient-deficient. Reports indicate that nutrient limited conditions can trigger expression of various genes, including several encoding outer membrane proteins, which may serve as virulence factors, and may contribute to the regulation of colonization factors. See e.g., Paustian et al., J. Bacteriol. 2002, Vol. 184:3734-3739. It is contemplated herein that these outer membrane proteins may also serve as phage receptors. Thus, in a particular embodiment, the methods of the present invention contemplate culturing environmental samples comprising bacteriophage and a bacterial pathogen in minimal medium. The term "minimal medium" is familiar to one of skill in the art and includes but is not limited to limiting the carbon source, available proteins and/or amino acids, fatty acids, vitamins, and crude extracts (e.g. yeast extracts, brain extracts, etc.) Different types of minimal media may be obtained from commercial vendors and include, e.g., M9 minimal media (Thermo Fisher Scientific) and custom derivatives thereof.

Additionally, nutrients may be added that mimic the available nutrients in a host environment, such as using phosphorylated sugars, triglycerides, or DNA as carbon sources, and adding iron in the form of heme are examples of supplying nutrients as they exist in the host-environment. A variety of different cell culture media (commercially available or custom formulated) may be used.

Regardless of how effective conditional cultures are in generating host-adapted bacteria, using conditional cultures according to the instant invention may result in bacterial gene expression changes and/or produce direct actions on the phage particles themselves that will alter phage competition dynamics across the conditions, thus producing differentially enriched populations of phages from the original environmental sample across the conditional cultures, allowing for enhanced or even maximal phage harvesting from the original environmental sample.

pH

Possible virulence factors for bacterial pathogens, e.g., enteric pathogens, may be induced by an acidic environment, e.g., *Heliobacter pylori* virulence factors may be influenced by the pH of the culture medium. See Merrell et al., Infect. Immun. 2003 Vol. 71: 3529-35379; Karita M. et al. Infect. Immun, 1996 64:4501-4507; Ang et al, infect. Immun. 2001 69:1679-1686. Thus, it is contemplated herein that modifying the pH of culture conditions may be used to mimic an in vivo infection. In a particular embodiment, the pH of the medium may be titrated below about 7.2, e.g., to about pH 5.5 or below, and/or within a range of 5.5-8.5. In addition to subjecting the pathogens to acid stress, a major endogenous buffer in the mammalian host is the carbonic-acid-carbonate buffering system in blood. Using this buffering system in vitro may better mimic the host environment.

Incubation Conditions

In various embodiments, conventional in vitro bacterial culture conditions may be modified to more closely resemble conditions that bacteria will encounter during an in vivo infection of a host. These conditions may be mimicked by modifying not only the formulation of the culture media, but also by modifying the cell culture incubator conditions, e.g., the temperature, humidity, osmotic pressure, carbon dioxide, and oxygen content of the incubator atmosphere as discussed in detail below.

Temperature

Conventionally, bacterial cultures are typically maintained at temperatures which provide optimum growth conditions. Typically, for pathogenic bacteria this is 37° C. (98.6 F). While the conditional cultures of the instant invention may be modified in other ways and still cultured at 37° C., it is also contemplated herein, however, that different repertoires of bacterial gene expression may be induced by manipulating the culture temperature above or below 37° C. (e.g. up to about the maximum growth temperature or down to about the minimum growth temperature). This genetic response to temperature change may be useful to enhance the expression of one or more virulence factors in a bacterial pathogen, or may result in other surface feature changes thereby altering potential phage receptors. Specifically, heat-stress is used by the host during infection and the development of fever. Growing the bacterial cultures at 42° C. alone or in combination with other culture changes, may produce physiological conditions that better mirror those of a bona-fide infection. Phages isolated on these bacteria may have better therapeutic potential. Data provided in the examples include experiments performed at 37° C. as well as 25° C. (room temperature), Carbon Dioxide and Oxygen One of skill in the art will appreciate that bacteria are typically classified as aerobes, microaerophiles, obligate anaerobes, aerotolerant, and facultative organisms. To this end, it is contemplated herein that the methods of the present invention may comprise modifying the level of oxygen and/or carbon dioxide in bacterial cultures to more closely mimic in vivo infections of obligate anaerobes or microaerophiles. Indeed, it has been reported that microaerophilic conditions are associated with the activation of *H. pylori* virulence genes. See Cottet et al., J. Biol. Chem., 2002 277:33978-339986. Additionally, bacterial pathogens growing in localized wounds, in organs (including the liver and spleen), or systemically in blood are actually in microaerophilic environments. Thus, mimicking this condition will better mirror the oxygen tension present in an actual infection. Thus, it is contemplated herein that in various embodiments, the conditional cultures of the instant invention may be grown in incubators from about 0-20% $O_2$, and/or from about 0-7% $CO_2$, particularly at less than 2% $O_2$ and/or at 5% $CO_2$.

Biofilm and Planktonic Growth

One of skill in the art will appreciate that conventional phage harvesting methods rely on the use of planktonic cells to isolate and harvest phages. Literature reports indicate, however, that gene expression patterns are different in biofilms and in planktonic bacteria. See Tremoulet et al., FEMS Microbiol Lett 2002 210:25-31. Thus, it is contemplated herein that gene expression patterns that mirror infection could occur not only in cultures of planktonic cells that have host-like surface features, but also in bacteria growing in biofilms. Thus, both types of cultures are encompassed according to the methods of the instant invention.

Indeed, bacteria growing in numerous types of infections, including wound infections, surgical hardware associated infections, and even some organ infections, are known to grow as a biofilm. Additionally, the biofilm may also confer antibiotic resistance, exacerbating the infection. Thus, in a particular embodiment, it is contemplated herein that the methods of the instant invention comprise using bacteria first grown in a biofilm (e.g., on biotic and/or abiotic surfaces), to drive gene expression and surface protein expression to mirror the bacterial surface features present in a biofilm growing during an actual infection, and then using that biofilm for phage isolation in the methods of the invention.

In a particular embodiment, the culture condition induces the formation of bacterial biofilm. These culture modifications include but are not limited to increasing culture incubation time up to several days, e.g., from about 18 hours to about 7 days (contrary to typical culture growth of 18 hours or less), not agitating the culture, and modifying the media to one that supports biofilm production, e.g., pro-biofilm media often contains stronger buffers to detoxify acidic waste products and the increased concentration of carbon sources. In another embodiment, biofilm formation may be induced by culturing the bacteria on biotic surfaces and or abiotic surfaces such as collagen coated surfaces, bone, and surfaces coated with host cells lysates, as well as stainless steel, titanium, plastic, and aluminum. In a particular embodiment, biotic surfaces may comprise complex host extracts. As understood herein, "complex host extracts" may comprise, e.g., crude, unpurified homogenates/lysates of tissue culture cells, e.g., mouse and human cells, and/or homogenized muscle/bone from mice and rats.

Biofilm matrix material and bacterial surface features within the biofilm can change as the biofilm is gown on different surfaces. Thus, in a particular embodiment, it is contemplated herein that the methods of the instant invention may comprise culturing bacteria on different biotic and abiotic surfaces in order to more closely reflect conditions associated with both body surface biofilm infections, as well as surgical hardware associated infections in vivo.

Measuring Gene Expression

In a particular embodiment, it is contemplated herein that modifying the bacterial culture conditions according to the methods of the instant invention may trigger an expression pattern of one or more genes in said infectious pathogenic bacteria in vitro that are similar to an expression pattern of said one or more genes in said infectious pathogenic bacteria during infection of said host in vivo. Specifically, it is contemplated herein that by modulating culture conditions to more closely resemble the physiological and biochemical environment in vivo, gene expression in cultured bacteria cells may be manipulated to more closely reflect the bacterial proteome in viva, including the surface features that may serve as phage receptors in vivo.

As used herein, the phrase, "trigger an expression pattern of one or more genes" and like terms refers to the ability of one or more culture conditions to drive the expression of one or more genes in the cultured bacteria. This includes the ability of the culture condition(s) to upregulate or downregulate gene expression levels. For example, as discussed above, it is contemplated herein that the methods of the instant invention may promote or upregulate the expression of genes encoding bacterial surface features found in host-adapted bacteria, but not expressed in conventional cultures. It is also contemplated herein that the methods of the instant invention may turn off or reduce the expression of one or more bacterial surface proteins that may act as phage receptors in vitro, but actually do not play a major role in the interaction between phage and bacteria in viva as in viva these receptors are also downregulated and/or are not present. It is contemplated herein that the down-regulation of such "decoy" receptors in the conditional cultures of the instant invention may facilitate the identification of clinically more useful phages, e.g., by permitting binding to less abundant and/or obscure bacterial surface receptors that are present during both in vitro and in vivo growth.

Notably, the fact that a phage may not infect a bacterial strain grown in vitro, or may not infect in a manner that would predict clinical utility, but can nevertheless provide a clinical benefit against the same bacterial strain grown in vivo, or under host-like conditions, is at odds with current and conventional methods for identifying phages for therapeutic use. In addition, according to the tenets of conventional methods of phage harvesting, obscure bacterial surface receptors might be deemed of little interest when phages are identified in vitro. Indeed, it is against all current strategies used in vitro for phage harvesting to purposefully get rid of receptors on the surface of bacteria that allow for robust phage predation in vitro. In contrast, in a particular embodiment, the methods of the instant invention are designed to induce the expression of bacterial surface receptors which do not allow for phage predation in vitro.

It is also contemplated herein that, in a particular embodiment, harvesting wild-phages from conditional cultures using the methods of the present invention may permit the isolation of phages that use atypical receptors and/or which will have different host ranges relative to phages isolated from traditional (e.g., 37° C.) cultures. While of scientific interest, and might be analyzed using conventional methods, it is not necessary to characterize the changes on the bacterial surface which occur when the bacteria are cultured according the methods of the instant invention, as the objectives of the instant invention include improved methods of isolating phages from environmental sources, including phages which may be more likely to have a therapeutic use against infectious pathogenic bacteria in vivo. Indeed, it is understood herein that phages identified according to the methods of the instant invention may be used to provide enhanced therapeutic efficacy without necessarily first understanding the mechanism of action behind the increased therapeutic efficacy.

In fact, one of skill in the art will appreciate that the high-throughput and empirically determined results provided according to the methods of the instant invention run completely counter to current methods. Nevertheless, so long as the phages isolated according to the methods of the instant invention are characterized as safe for human use, they can be used to build robust and diverse phage libraries directed against infectious pathogenic bacteria, including but not limited to MDR. ESKAPE bacterial pathogens selected from the group consisting of *Enterococcus faecium, Staphylococcus aureus, Klebsiella pneumoniae, Acinetobacter baumannii, Pseudomonas aeruginosa*, and *Enterobacter* spp. It is contemplated herein that these phage libraries may be created and the phages used for various industrial and/or therapeutic purposes, e.g., in library-to-cocktail and/or other therapeutic phage modalities according to conventional methods. See, e.g., U.S. Ser. No. 15/628,368, the entire contents of which are incorporated by reference herein.

Methods of Measuring Effects of Phage on Bacteria

Methods for identifying the ability of a phage to "infect and kill" target bacteria in the conditional cultures of the instant invention may be performed using conventional methods. For example, the assay may comprise determining the effectiveness of one or more phages to prevent bacterial growth in the conditional culture media (which otherwise supports robust bacterial growth.) This may include, for example, performing conventional phage plaque assays or spot assays where the effectiveness of phage or various phage combinations to prevent bacterial growth can be evaluated in conditional cultures on solid agar or semi-solid medium media. Such techniques are familiar to one of skill in the art. See, e.g., Sambrook, J., E. F. Fritsch and T. Maniatis (1989). "Molecular Cloning: A Laboratory Manual. 2nd ed." Cold Spring Harbor Press, Cold Spring Harbor, N.Y.

Other methods for identifying the ability of a phage to "infect and kill" target bacteria may comprise the use of "phage efficacy assays" which comprise growing cultures of a targeted bacterial pathogen with individual phages or phage combinations and analyzing bactericidal activity against the targeted bacterial pathogen, wherein a suitable delay in bacterial growth and/or the lack of appearance of phage-resistant bacterial growth in the culture indicates that the phage(s) may be therapeutically effective against the targeted bacterial pathogen in vivo.

High-throughput methodologies comprising the use of microliter plates and liquid media for running multiple simultaneous assays and cultures are also contemplated herein. For example, a clinical isolate of a bacterial pathogen may be raised in conditional cultures or as biofilms as described herein, and then a culture inoculum may be aliquoted to phage dilutions in wells of a 96 well-plate, or the biofilm is first grown in the plate. The interaction between the bacteria and phage is then monitored for evidence of bacterial growth delay, and or destruction of the biofilm. In a particular embodiment, the delay in bacterial growth and/or the lack of appearance of phage-resistant bacterial growth, or the destruction of the biofilm, may be monitored comprising the use of a high-throughput photometric assays and liquid media, and/or microscopic analysis of biofilm destruction. In particular embodiments, the photometric assay may be, e.g., fluorescence, absorption, or transmission assays. In a particular embodiment, the photometric assay comprises a step wherein an additive such as tetrazolium dye is used to cause and/or enhance the photometric signal detection.

For example, in a particular embodiment, such assays include phage efficacy assays monitoring the delay in bacterial growth, called a growth "hold-time," which can be used to determine the lytic activity of individual phages or compounded phage cocktails using an automated, high throughput, indirect liquid lysis assay to evaluate phage bactericidal activity using an OMNILOG system (Henry M, et al. 2012, Bacteriophage 2:159-167). Such assay is described in detail in U.S. Ser. No. 15/628,368, the entire contents of which are incorporated by reference herein. Biofilm destruction assays may be monitored by direct microscopy or indirect measurements using crystal violet staining followed by photometric analysis according to conventional methods.

As used herein, the terms "desirable delay in bacterial growth", "suitable delay in bacterial growth", "growth hold time", "lack of appearance of phage-resistant bacterial growth", "biofilm destruction" and like terms is understood to relate to the effectiveness of a phage, phage combination, or phage cocktail to prevent bacterial growth for a given amount of time in culture or to degrade biofilm structures in culture. In a particular embodiment, this includes bacterial growth in the liquid culture environment as described in U.S. Ser. No. 15/628,368. Typically, in this assay, growth hold-time indicative of a promising phage is from about 4 to about 8 hours. In a particular embodiment, the growth hold time of a promising phage cocktail, assembled from individual phages deemed as promising, may be a minimum hold-time of about 12 hours to about 18 hours or longer without limit. In other particular embodiments, the growth hold time of a phage or phage cocktail may be from about 15, 16, 17, 18, 19, or 20 hours. In another embodiment, cocktail hold-times of less than 12 hours may have therapeutic efficacy.

In yet another embodiment, the growth hold-time of a promising individual phage may be zero or undetectable and only when this type of phage is included with another phage deemed to be promising, or as a new constituent of a cocktail deemed to be promising, will the activity and necessity of such a phage become detectable. In such situations, phages of this type, which have undetectable or nearly undetectable activities on their own, can surprisingly add to a synergistic hold-time when included in promising phage cocktails.

It is contemplated herein that the methods of the instant invention can be used to identify a phage or a phage combination, including synergistic phage combinations, which can produce a complete or nearly complete growth arrest of the bacterial pathogen. This may be evident from a growth hold time from about 16-48 hours or more.

One of skill in the art will appreciate that promising growth hold times, including minimum hold times, and growth hold times indicative of complete or nearly complete growth arrest, may vary depending on the species of bacteria, e.g., some bacterial species typically grow more slowly than other bacteria. Promising growth hold times of bacteria under investigation may be easily discerned according to the methods of the instant invention without undue experimentation.

In addition to hold time in liquid cultures, biofilm destruction may also be monitored and individual phages, phage cocktails, synergistic phage cocktails, and promising phages with no detectable activity on their own, may be scrutinized as before as with liquid cultures, but the read out for potential therapeutic efficacy here is the ability of individual phages or phage cocktails to degrade or destroy biofilms. Biofilm destruction is scored by direct monitoring using microscopy or indirect measurements using staining techniques according to conventional methods.

As understood herein, a "subject", "subject in need thereof" and like terms encompass any organism, e.g., any animal or human, that may be suffering from a bacterial infection, particularly an infection caused by a MDR bacteria.

As used herein, a "clinical isolate" is a pathogenic bacteria harvested from human or animals during course of pathogenesis or gradual progression of a specific disease, e.g., an infectious bacterial pathogen that was isolated from a bona-fide human infection.

As understood herein, a "bona-fide human infection" refers to a bacterial infection, which produces pathogenesis in humans, including, e.g., a symptomatic infection that requires medical intervention, including culturing the infectious bacterial strain.

As used herein, the term "infectious pathogenic bacteria" refers to a bacterial strain capable of causing disease or a detectable pathology within a human or animal. In a particular embodiment, the methods of the instant invention may be employed with any bacterial pathogen, including but not limited to pathogens that display differential gene expression in a host vs in vitro growth. One of skill in the art will appreciate that all facultative pathogens do this, including but not limited to, all of the ESKAPE pathogens. Thus, bacteria that may be treated include, but are not limited to the "ESKAPE" pathogens (*Enterococcus faecium, Staphylococcus aureus, Klebsiella pneumonia, Acinetobacter baumannii, Pseudomonas aeruginosa*, and *Enterobacter* sp), which are often nosocomial in nature and can cause severe local and systemic infections. Specifically, these include, e.g., methicillin-resistant *Staphylococcus aureus* (MRSA); vancomycin-resistant *Enterococcus faecium* (VRE); carbapenem-resistant *Klebsiella pneumonia* (NDM-1); MDR-*Pseudomonas aeruginosa*; and MDR-*Acinetobacter baumannii*.

Among the ESKAPE pathogens, *A. baumannii* is a Gram-negative, encapsulated, opportunistic pathogen that is easily spread in hospital intensive care units. For example, *A. baumannii* infections are typically found in the respiratory tract, urinary tract, and wounds. Many *A. baumannii* clinical isolates are also MDR, which severely restricts the available treatment options, with untreatable infections in traumatic wounds often resulting in prolonged healing times, the need for extensive surgical debridement, and in some cases the further or complete amputation of limbs. Notably, blast-related injuries in military populations are associated with significant tissue destruction with concomitant extensive blood loss and therefore these injuries are at high risk for infectious complications. One of skill in the art will appreciate that given the ability for *A. baumannii* and other MDR ESKAPE pathogens to colonize and survive in a host of environmental settings, there is an urgent need for new therapeutics against these pathogens.

Any type of bacterial contamination may be treated using the methods, phage libraries, and compositions of the instant invention. Particularly, bacterial infections to be treated using the compositions, libraries, and methods of the instant invention may include any infection by a bacterial pathogen that poses a health threat to a subject. In a particular embodiment, bacteria for treatment according to the methods of the present invention include, but are not limited to, multidrug resistant bacterial strains. As understood herein, the terms, "multidrug resistant", "multi drug resistant", "multi drug resistance", "MDR" and like terms may be used interchangeably herein, and are familiar to one of skill in the art, i.e., a multidrug resistant bacteria is an organism that demonstrates resistance to multiple different antibacterial drugs, e.g., antibiotics; and more specifically, resistance to multiple different classes of antibiotics. It is understood herein that bacterial infections to be treated comprise bacteria in biofilm and/or planktonic growth modes.

One of skill in the art will appreciate that bacterial infections to be treated using the compositions, libraries, and methods of the instant invention include any type of bacterial infection in a subject. These include, for example, not only infections that may be associated with wounds, but also non-wounds, e.g., infections that might arise without underlying trauma or any other type of bodily injury, traumatic or otherwise. These infections may include local infections, e.g. a respiratory infection or an internal or external abscess that progresses to a systemic infection. Infections that may be treated according to the methods of the instant invention also include infected surgical wounds, e.g., "post-surgical" infections that may arise in a subject after and/or resulting from a surgical procedure or any other kind of medical or surgical treatment or intervention, e.g., a catheterization procedure, or surgical implantation of a medical device, prosthetic, or other foreign object into a subject, etc.

One of skill in the art will appreciate the myriad other therapeutic uses for the compositions of the instant invention given that the compositions can be administered both topically and systemically, e.g. via IV or IM injections, or injected into the peritoneal cavity. They may be provided as aerosols, or in any other manner that is pharmaceutically suitable. The types of infections that can be treated also include, for example, infections associated with burns, ulcers, systemic bacteremia, septicemia, inflammatory urologic disease, infections associated with cystic fibrosis, abscesses, empyema, suppurative lung diseases, as well as infections in other internal organs, including but not limited to infections in the liver, spleen, kidney, bladder, lungs etc.

As used herein, the term "sample comprising phages", "a sample of phages" and like terms refer to a sample comprising phages obtained from any source. It is understood by those of skill in the art that phages are omnipresent; one can expect phages to be present in any sample taken from a place where bacteria exist. This includes but is not limited to samples obtained from nature as well as man-made sources. The sample may comprise any number and combination of "wild" phages (phages found in nature), previously unidentified phages, or phages that have been previously isolated. Samples comprising phages obtained from academia and commercial or noncommercial sources are included in this definition. Thus, as understood herein, a "sample comprising phages" for assay according to the methods of the instant invention may be obtained by harvesting phages from a variety of diverse environmental sources. Such samples may comprise more than one phage, i.e., the sample may comprise mixed phages. Samples of phages may be taken from a wide variety of different places where phage may be found in the environment, including, but not limited to, any place where bacteria are likely to thrive. In fact, phages are universally abundant in the environment. Samples of phages include but are not limited to samples acquired from diverse environmental sources, including samples which comprise uncharacterized "wild phages", as well as samples of characterized phages that may be obtained from laboratories or commercial vendors.

One of skill in the art will appreciate the myriad sources of phage that may be assayed according to the methods of the instant invention. For example, possible sources include, but are not limited to, natural sources in the environment such as soil and water, as well as man-made sources such as untreated sewage water and water from waste-water treatment plants. Clinical samples from infected subjects (e.g., human patients, animals or any other species) may also serve as a source of phage. In a particular embodiment, diverse environmental sources of phage may be selected from the group consisting of soil, water treatment plants, raw sewage, sea water, lakes, rivers, streams, standing cesspools, animal intestines, human intestines, manure or other fecal matter, organic substrates, biofilms, and medical/hospital sources. Phage may be sourced anywhere from a variety of diverse locations around the globe, e.g., within the US and internationally.

Bacteriophage and Bacterial Libraries

As discussed above, due to the upregulation and downregulation of different proteins within bacteria grown in host-like conditions, it is contemplated herein that by harvesting wild phages from conditional cultures, it will be possible to isolate phages from the environment that use atypical receptors and will have different host ranges relative to phages isolated from traditional 37° C. cultures. Ideally, the methods of conditional phage isolation as contemplated herein will select for phages that are better suited to infecting bacteria growing within a mammalian, e.g., human host, and thus permit the creation of therapeutic phage cocktails which can provide enhanced therapeutic efficacy.

In view of the foregoing, the identification of phages according to the methods of the instant invention also permits the creation of phage libraries of enhanced richness. In particular embodiments, the methods described herein permit the creation of enhanced phage libraries against bacterial pathogens of interest comprising individual phages that have distinct but overlapping host ranges. Such a library allows for maximal coverage of clinically relevant bacterial strains, including MDR bacterial pathogens.

Thus, in another aspect, the invention relates to bacteriophage libraries comprising the bacteriophage identified according to the methods of the instant invention. Specifically, it is contemplated herein that the host range and plaque morphology of phages grown up in conditional cultures may be compared to that of phages harvested under classical conditions and used to compile a robust library of diverse bacteriophage against different bacterial pathogens, including bacteriophage with enhanced propensity to infect and kill infectious bacterial pathogens in vivo. In a particular embodiment, the development of a large globally-sourced library of phages 200-500 phages/pathogen) against MDR pathogens is contemplated herein. In a particular embodiment, the library is against an MDR ESKAPE bacterial pathogen selected from the group consisting of *Enterococcus faecium, Staphylococcus aureus, Klebsiella pneumoniae, Acinetobacter baumannii, Pseudomonas aeruginosa,* and *Enterobacter* spp. The creation of such libraries requires diverse collections of MDR ESKAPE pathogens and, ideally, access to extremely contaminated water sources. In this regard, large collections of diverse MDR ESKAPE pathogens have already been obtained and are available for use according to the methods of the instant invention as hosts for phage isolation; contaminated environmental water sources may be collected from a diversity of sources. The host ranges of the phages in these libraries will be characterized and phages with broad host ranges will also be sequenced.

One of skill in the art will appreciate that phages exist as a population centered-around a consensus genome sequence, but there is an n-dimensional distribution around that consensus sequence. Thus, in a particular embodiment, it is contemplated herein that starting with a diverse phage library, particularly in high concentration, will create an enormous level of phage sequence diversity to bring to bear against the problem of MDR resistance. As discussed above, it is contemplated herein that the phage libraries of the instant invention may be sourced from around the globe. This is particularly relevant with regard to the design of phage therapeutics to treat military service members who routinely encounter bacterial pathogens from global sources. Indeed, phages to those global pathogens are best found in the environment adjacent to the site of the acquired infection. Thus, it is contemplated herein that by harvesting phages from a variety of sources from around the globe, and assaying these phages using conditional cultures according to the methods of the instant invention, large and genetically diverse bacteriophage libraries may be successfully generated for use in creating phage therapeutics.

The global and conditional phage libraries created here can also serve as powerful starting materials for the development of population level cocktails, engineered phages, and augment the library-to-cocktail approach, indeed, it is contemplated herein that all current methodologies of developing therapeutic phage, whether one is developing population level cocktails, engineered phages, or employing a library-to-cocktail personalized therapeutic approach, would benefit from methods designed to identify additional phage that can infect and kill bacterial pathogens under infection-associated physiological conditions, and thus provide the means to create more robust phage libraries and therapeutics against these pathogens. Thus, in particular embodiments, phage libraries of the instant invention include but are not limited to libraries of phage against MDR bacterial pathogens, including e.g., ESKAPE phage libraries. It is contemplated herein that these new, more robust libraries can be created by using the methods of the instant invention, and can serve as rich starting resources for the continued development of other phage-based therapeutic modalities.

As discussed herein, the methods of the instant invention include creating unique and expanding sets of clinically relevant bacterial pathogens, including but not limited to MDR bacterial strains, and using these local MDR bacterial strains isolated from the sources proximal to the phage harvesting efforts to increase the chances of finding diverse and appropriate phages.

One of skill in the art will appreciate that, in addition to the loss of receptor and receptor mutations that can block phage infectivity, bacterial strains can become resistant to phage-infection downstream of phage attachment and genome injection. In addition, phage resistance is to be expected during therapy. However, developing resistance to one phage may sensitize the strain to another phage, and this resistance/sensitization is extremely difficult to predict a priori. Phage libraries are tools that enable the empirical selection of phages that work together through rounds of resistance/sensitization.

Compositions and Methods of Treatment

It is contemplated herein that the creation of large libraries of phages that are capable of infecting and killing bacterial cultures which are phenotypically more consistent with bacterial pathogens in vivo i.e., bacteria which in vivo display a host-adapted gene expression pattern and surface-feature repertoire, may effectively facilitate the enhanced development of numerous phage therapeutic modalities, including natural phage products, as well as phages engineered to carry antimicrobial cargo or to possess expanded host-range. Thus, in another aspect, the instant invention relates to compositions, including pharmaceutical compositions, comprising one or more phages identified according to the methods of the instant invention and which demonstrate enhanced therapeutic efficacy. In a particular embodiment, the composition is a "phage cocktail" comprising a plurality of phages against infectious pathogenic bacteria.

The compositions of the instant invention, in a pharmaceutically acceptable dosage form, may be administered to a subject in a manner as deemed appropriate by an attending physician. In particular embodiments, the compositions are therapeutically effective compositions of very high titer and very high purity, or of high titer and high purity, which are not found in nature. Such degrees of purity and titer are familiar to one of skill in the art, and are discussed at length in U.S. Ser. No. 15/628,368, the entire contents of which are incorporated by reference herein.

Indeed, it is contemplated herein that the compositions produced according to the methods of the instant invention may be unique in composition as well as uniquely effective compared to compositions made according to conventional methods. As used herein, the term "composition" encompasses pharmaceutical compositions comprising a plurality of purified phages, e.g., a composition of the instant invention may be a "phage cocktail."

"Pharmaceutical compositions" are familiar to one of skill in the art and typically comprise active pharmaceutical ingredients formulated in combination with inactive ingredients selected from a variety of conventional pharmaceutically acceptable excipients, carriers, buffers, diluents, etc. Methods of formulating pharmaceutical compositions are familiar to one of skill in the art.

The term "pharmaceutically acceptable" is used to refer to a non-toxic material that is compatible with a biological system such as a cell, cell culture, tissue, or organism. Examples of pharmaceutically acceptable excipients, carriers, buffers, diluents etc. are familiar to one of skill in the art and can be found, in *Remington's Pharmaceutical Sciences* (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

As understood by one of skill in the art, the type and amount of pharmaceutically acceptable additional components included in the pharmaceutical compositions of the instant invention may vary, e.g., depending upon the desired route of administration and desired physical state, solubility, stability, and rate of in vivo release of the composition.

As contemplated herein, the pharmaceutical compositions of the instant invention comprise an amount of phage in a unit of weight or volume suitable for administration to a subject. In this regard, it is noted herein that using conventional methods, isolated phages are directed against in vitro adapted bacteria, thus conventional methods typically employ very high titer of phages for therapeutic use. In contrast, it is contemplated herein that because phages identified using the methods of the instant invention better match the in vivo physiology of the targeted infections pathogenic bacteria, such phages may be able to be used for therapeutic purposes in much lower titers.

The volume of the composition administered to a subject (dosage unit) will depend on the method of administration and is discernible by one of skill in the art. For example, in the case of an injectable, the volume administered typically may be between 0.1 and 1.0 ml, e.g., approximately 0.5 ml. In another embodiment, up to 10 ml may be delivered in conjunction with a saline IV.

For administration by intravenous, cutaneous, subcutaneous, or other injection, a pharmaceutical formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art. It is understood herein that isotonic properties of Ringer's solution make a suitable buffer for phage cocktails, while "SM buffer" may be used for phage dilution and storage. Of particular interest with phage therapeutics is the removal or limitation of host bacterial components from the phage cocktail preparation that may have deleterious effects on the host, which include but are not limited to LPS, peptidoglycan, bacterial toxins, and bacterial DNA. Therapeutic cocktail preparations can be designed to contain these kinds of materials in amounts below acceptable limits.

In another aspect, the present invention relates to methods of treating a bacterial infection comprising administering to a subject in need thereof an effective amount of a composition comprising one or more phages identified according to the methods of the instant invention. In a particular embodiment, the composition is a pharmaceutical composition.

As understood herein, a "subject in need thereof" includes any human or animal suffering from a bacterial infection, including but not limited to a multidrug resistant bacterial infection.

As understood herein, terms such as "effective amount" and "therapeutically effective amount" of a composition of the instant invention, refer to an amount of a composition suitable to elicit a therapeutically beneficial response in the subject, e.g., by eradicating a bacterial pathogen in the subject and/or altering the virulence or antibiotic susceptibility of surviving phage-resistant bacterial pathogens and/or by providing an added benefit when a composition of the instant invention is simultaneously administered with either effective and/or ineffective antibiotics. Such response may include e.g., preventing, ameliorating, treating, inhibiting, and/or reducing one of more pathological conditions associated with a bacterial infection. One of skill in the art will appreciate that it is desirable that the initial dose of a phage cocktail of the instant invention be sufficient to control the bacteria population before it reaches a lethal threshold. Animal models suggest that $10^9$ to $10^{11}$ pfu/ml phage particles per dose would likely be the maximum dosage tenable based on protein load presented acutely to the liver in an adult (which would be scaled down in a pediatric population, i.e., EU limited $10^5$ dosing discussed in the below examples). It is suspected that this is a sufficient acute bolus to reduce the bacterial burden sufficiently to potentiate an immune response. Notably, phage "viremia" may be measured in the blood after administration. Animal models suggest that viremia is quite transient given the host immune response and sequestration in the reticuloendothelial system (liver and spleen).

Suitable effective amounts of the compositions of the instant invention can be readily determined by one of skill in the art and can depend upon the age, weight, species (if non-human) and medical condition of the subject to be treated. In addition, one of skill in the art will appreciate that the type of infection (e.g., systemic or localized), and the accessibility of the infection to treatment may also impact the dosage amount that is deemed effective. One of skill in the art will appreciate that initial information may be gleaned in laboratory experiments and an effective amount of a composition for humans subsequently determined through dosing trials and routine experimentation.

It is contemplated herein that the compositions of the instant invention may be administered to a subject by a variety of routes according to conventional methods, including but not limited to systemic, parenteral (e.g., by intracisternal injection and infusion techniques), intradermal, transmembranal, transdermal (including topical), intravesicular, intramuscular, intraperitoneal, intravenous, intraarterial, intralesional, subcutaneous, oral, and intranasal (e.g., inhalation of an aerosolized composition) routes of administration. Administration can also be by continuous infusion or bolus injection.

In addition, the compositions of the instant invention can be administered in a variety of dosage forms. These include, e.g., liquid preparations and suspensions, including preparations for parenteral, subcutaneous, intradermal, intramuscular, intraperitoneal or intravenous administration (e.g., injectable administration), such as sterile isotonic aqueous solutions, suspensions, emulsions or viscous compositions that may be buffered to a selected pH. In a particular embodiment, it is contemplated herein that the compositions of the instant invention are administered to a subject as an injectable, including but not limited to injectable compositions for delivery by intramuscular, intravenous, subcutaneous, or transdermal injection. Administration by inhalation of an aerosolized composition is also contemplated herein. Such compositions may be formulated using a variety of pharmaceutical excipients, carriers or diluents familiar to one of skill in the art.

In another particular embodiment, the compositions of the instant invention, and/or pharmaceutical formulations administered in conjunction therewith, e.g., antibiotics, may be administered orally. Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients described herein, including but not limited to mannitol, lactose, starch, magnesium stearate, sodium saccharine, cellulose, and magnesium carbonate.

In a particular embodiment, it is contemplated herein that a composition for oral administration may be a liquid formulation. Such formulations may comprise a pharmaceutically acceptable thickening agent which can create a composition with enhanced viscosity which facilitates mucosal delivery of the active agent, e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser, nebulizer, or aerosol dispenser, are contemplated herein. Dosage forms suitable for rectal or vaginal delivery are also contemplated herein. Where appropriate, compositions for use with the methods of the instant invention may also be lyophilized and may be delivered to a subject with or without rehydration using conventional methods.

As understood herein, the methods of the instant invention comprise administering the compositions of the invention to a subject according to various regimens, i.e., in an amount and in a manner and for a time sufficient to provide a clinically meaningful benefit to the subject. Suitable administration regimens for use with the instant invention may be determined by one of skill in the art according to conventional methods. For example, it is contemplated herein that an effective amount may be administered to a subject as a single dose, a series of multiple doses administered over a period of days, or a single dose followed by one or more additional "boosting" doses thereafter. The term "dose" or "dosage" as used herein refers to physically discrete units suitable for administration to a subject, each dosage containing a predetermined quantity of the active pharmaceutical ingredient calculated to produce a desired response.

The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, intended goal of treatment, as well as the potency, stability, and toxicity of the particular composition. As understood by one of skill in the art, a "boosting dose" may comprise the same dosage amount as the initial dosage, or a different dosage amount. Indeed, when a series of doses are administered in order to produce a desired response in the subject, one of skill in the art will appreciate that in that case, an "effective amount" may encompass more than one administered dosage amount.

Diagnostics and Methods of Detecting Bacteria

Phage-based diagnostics and methods of detecting bacteria are also currently being developed for clinical and industrial applications. As discussed above, when a phage infects and replicates within its bacterial host, that phage can increase in titer from 10-100-fold in a single generation. The massive increase in phage titer is a specific "signal" that can be easily monitored by any number of techniques, including, e.g., classical phage titer counts, quantitative real-time PCR probing the phage genome or other reporter constructs, nucleic acid hybridization or other molecular assays, and fluorescence or immunofluorescence assays with labeled phage particles, etc. Phage diagnostics can discriminate between live bacterial cells and the presence of dead bacterial cells or cell debris since phages require a live host in which to replicate. Thus, phage-based diagnostics and methods of detecting bacteria are specific and powerful tools, but are constrained by the same requirements as phage therapeutics. Thus, in a particular embodiment, it is contemplated herein that the methods of the instant invention may be employed to create phage libraries for use in diagnostic applications, e.g., in a personalized, library-to-diagnostic approach. The methods of the instant invention provide new ways of harvesting diverse phages, and phages against conditionally adapted bacterial hosts, including host-adapted bacterial hosts, that will enable more powerful and specific diagnostics.

In particular aspects, it is contemplated herein that phage-based diagnostics may be used with clinical samples of a biotic origin, e.g., samples of blood, sputum, puss, etc., and industrial samples of an abiotic organ, e.g., swabs or otherwise wet samples from industrial machinery, food, makeup, and other pharmaceuticals, etc. Thus, identifying phages specific not only to a bacterial host, but to a bacterial host gown under very specific conditions, may be of particular importance to harvesting and library construction for the purposes of diagnostics. It is contemplated herein that the methods of the instant invention are adaptable and may be modified to address specific industrial diagnostic needs, e.g., employing phages identified according to the methods of the instant invention in methods of detecting bacterial contamination in various industrial applications (e.g. food industry) comprising altering conditions and/or additives to harvesting cultures, as needed by an end-user, without undue experimentation.

Kits and Articles of Manufacture

It is contemplated herein that reagents for conditional cultures disclosed herein, as well as compositions comprising phages identified according to the methods of the invention, may be provided to a user (e.g., a clinician treating a subject with a MDR bacterial infection, or attempting to diagnose a bacterial infection) in the form of a kit or other article of manufacture. Kits comprising pharmaceuticals or other agents or items for clinical use are familiar to one of skill in the art. Such kits may take many forms; typically, they comprise one or more packaging containers designed to safeguard the integrity and viability of the contents during transit and/or storage. In a particular embodiment, a kit of the instant invention may comprise one or more compositions and may further comprise one or more additional reagents or items for use therewith, e.g., buffers, diluents, etc. as well as instructions or other information describing and/or facilitating the administration of the kit contents. In various embodiments, in addition to active pharmaceutical ingredients, excipients, diluents, buffers, etc. the kits of the instant invention may comprise various articles or medical devices made from a variety of pharmaceutically acceptable materials or reagents for facilitating treatment of a subject. These include, but are not limited to, vials, syringes, IV bags, etc. Similar kits for diagnostic or industrial purposed are contemplated herein, the contents of which may be designed as proposed herein and determined by one of skill in the art.

The compositions of the instant invention may be administered to a patient alone, or in combination with one or more pharmaceutical agents in any manner or dosing regimen, e.g., before, after, or concomitantly with one or more other pharmaceutical or other therapeutic agent. Indeed, in a particular embodiment, optimal therapy may comprise the integration of bacteriophage therapy coupled to antibiotics and source control (if possible) in parallel with optimization of the host immune function. As understood by one of skill in the art, "source control" refers to treating the infection directly at the source of the infection in the subject, i.e., before the infection spreads systemically. As discussed above, in addition to exploiting bacteriophages for direct bacterial lysis, bacteriophages may act synergistically with antibiotics in vivo, while potentiating reversion of bacterial susceptibility to antibiotic classes.

Thus it is contemplated herein that administration of a therapeutic phage cocktail may stress the emergent bacterial strains such that the emergent bacterial strains regain sensitivity to one or more drugs, e.g., an antibiotic to which it previously demonstrated resistance. In addition, it is further contemplated herein that phage cocktails of the instant invention may be administered to a subject concurrently with one or more antibiotics or other drugs to enhance overall therapeutic efficacy, e.g., to produce a synergistic therapeutic effect. Thus, it is contemplated herein that phages, and specifically the compositions of the instant invention, may act synergistically with antibiotics, and/or potentiate reversion of pathogen susceptibility to antibiotic classes.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

Example 1

Using Conditional Cultures to Enhance the Isolation of Bacteriophages with Therapeutic Potential Against Multidrug Resistant ESKAPE Pathogens from the Peruvian Amazon The experiments provided below describe efforts to establish a diverse phage library against the ESKAPE pathogens, and demonstrate that using conditional phage isolation cultures can maximize the harvest of phages from environmental samples, increasing the diversity (host range) of a final library.

Materials and Methods

MDR Strains

MDR clinical isolates of *A. boumannii* (10 strains), *K. pneumoniae* (15 strains), *P. aeruginosa* (20 strains) and *S. aureus* (10 strains) were used to isolate phages from environmental water samples. These clinical isolates were collected in Iquitos, Peru, between 2011 and 2017 and each had a distinct isolation date and/or AST profile.

Phage Isolation and Purification

Environmental sewage water was collected in and around the Peruvian Amazon city of Iquitos. 3% w/v TSB-powder was directly mixed with 300 mL of the raw sewage and inoculated with 1 mL of each MDR strain in exponential phase, with 5 strains max per 300 mL to limit competition, and incubated at 37° C. shaking overnight. Following growth, 1.5 mL of the overnight bacteria-sewage culture was centrifuged at 12000 rpm for 1 min, and the phage-rich supernatant was filtrated with 0.22 µm filters to remove remaining bacteria. Serial dilutions of each sterile supernatant was then spotted (10 µL) onto lawns of each individual bacteria (TSB agar), and incubated at 37° C. overnight. Resulting single phage plaques were harvested by removing the plaque and agar plug with a Pasteur pipette and incubating the plugs in 300 µL of PBS for 60 min. The resuspended phages were then sterilized using 0.22 µm Spin-X centrifuge filters. The species-specific host range of all the isolated phages (1:5 dilution) were identified against the original bacterial strains used for phage isolation and additional MDR strains not used for isolation. Total strains for host-range analysis: 15 *A. baumannii*, 20 *K. pneumoniae*, 20 *P. aeruginosa*, and 20 *S. aureus*.

Conditional Culture Phage Isolation

Phage isolation was repeated with 10 MDR *K. pneumoniae* strains using the same sample of environmental water split into traditional TSB isolation cultures and TSB cultures containing 7.5% Fetal Bovine Serum (FBS). PBS is known to alter gene expression in bacterial pathogens. Phage isolation from the same water source using these two conditions was then compared, and the host ranges of the isolated phages was analyzed against the same 20 *K. pneumoniae* strains as before.

Results

Phage Harvesting Using Traditional Isolation

In total, 8 phages were found against 8 of the 10 *A. baumannii* (AB) strains, from 1 water source; 33 phages were found against 14 of the 15 *K. pneumoniae* (KP) strains, from 2 water sources; 17 phages were found against 16 of the 20 strains of *P. aeruginosa* (PA), from 2 water sources; 5 phages were found against 5 of the 10 strains of *S. aureus* (SA) from 1 water source.

Figure 2:
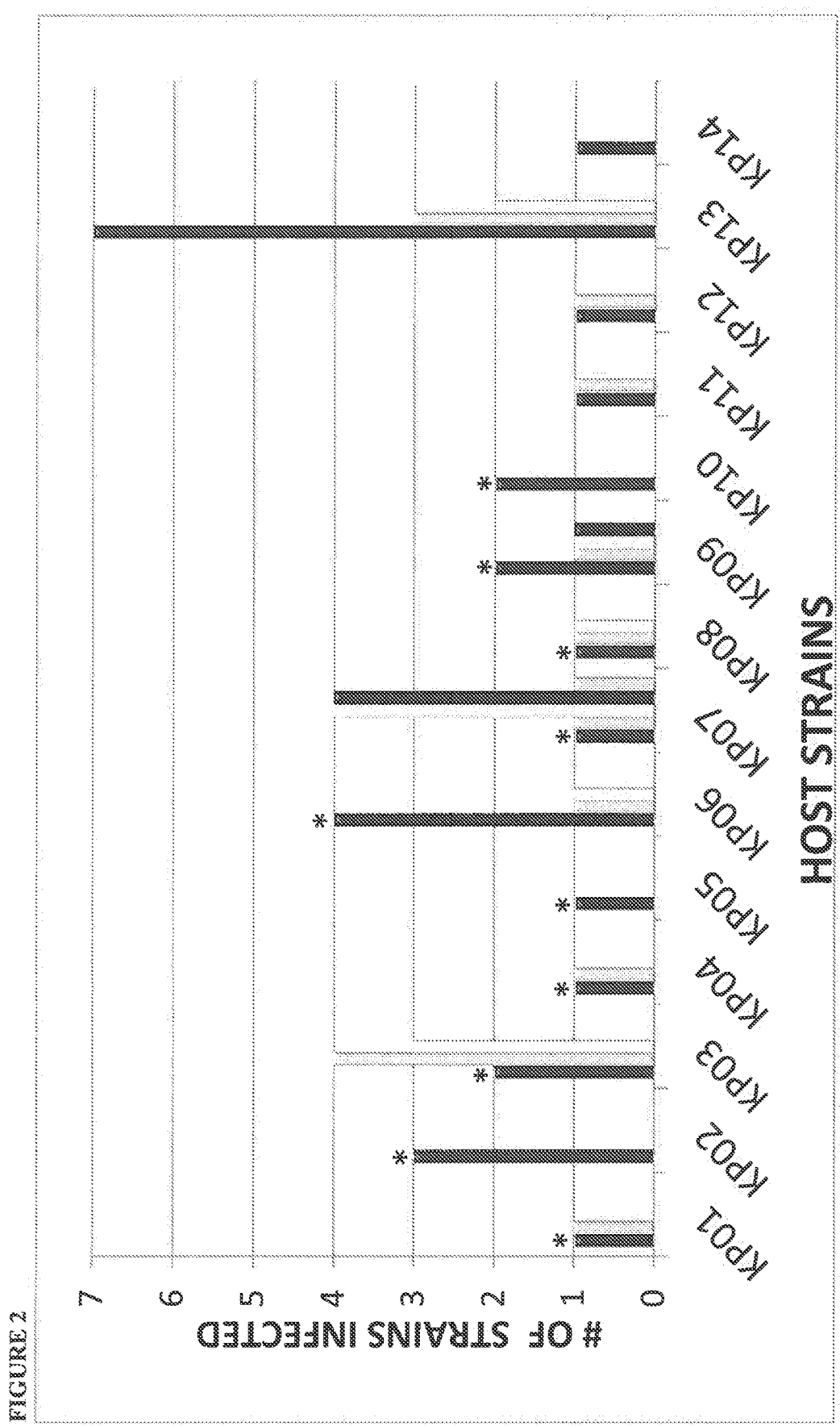
FIG. 2 depicts the host ranges of various *K. pneumoniae* (KP) phages isolated from the Peruvian Amazon in 2017. The symbol * indicates phages tested against only ten strains of KP, not twenty strains of KP. The different color bars represent different phages isolated against the same strain on the X axis. The magnitude of the bar is the total number of KP strains tested that each phage can infect.
Figure 3:
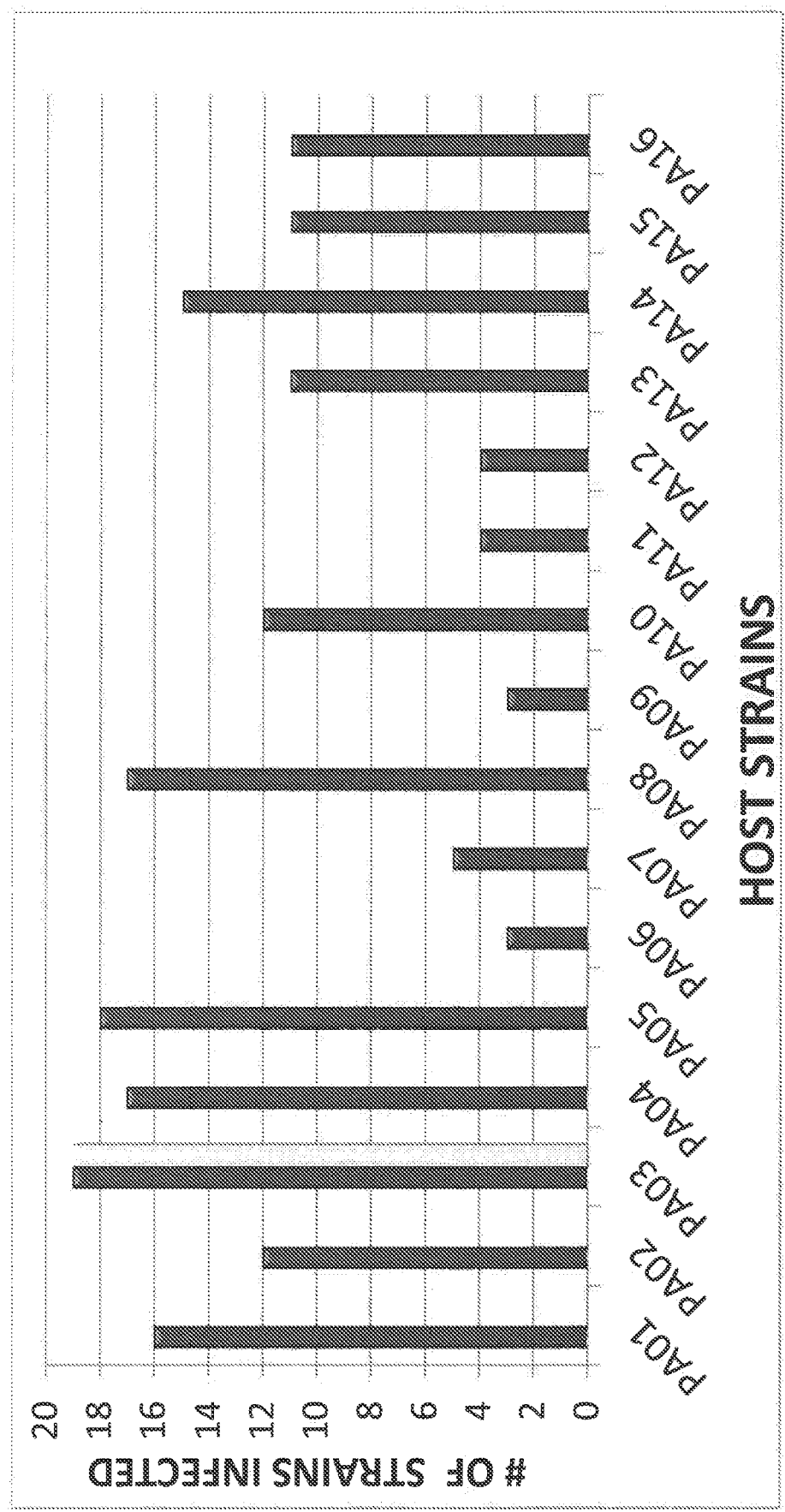
FIG. 3 depicts the host ranges of various *P. aeruginosa* (PA) phages isolated from the Peruvian Amazon in 2017. The different color bars represent different phages isolated against the same strain on the X axis. The magnitude of the bar is the total number of PA strains tested that each phage can infect.
Figure 4:
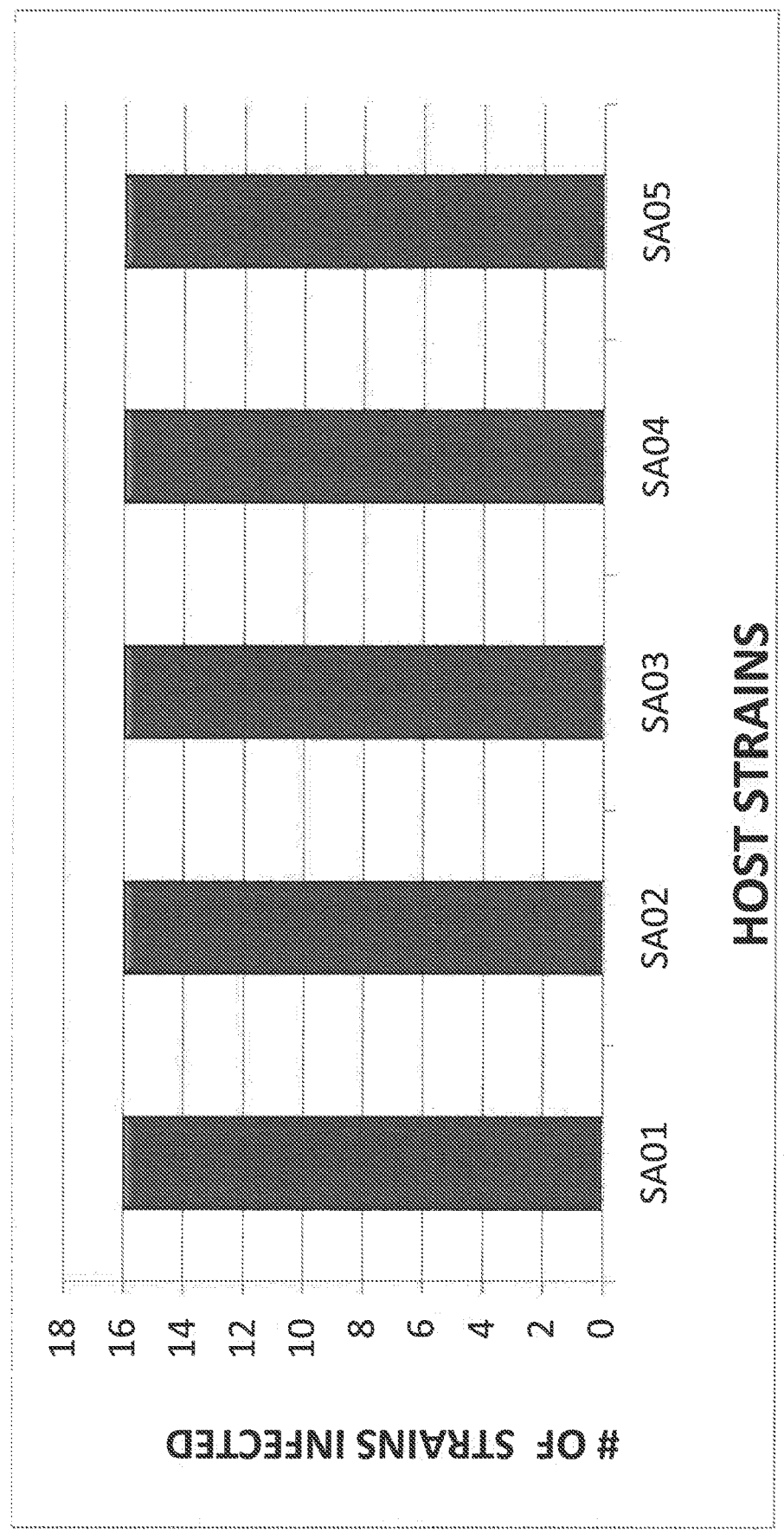
FIG. 4 depicts the host ranges of various *S. aureus* (SA) phages isolated from the Peruvian Amazon in 2017. The magnitude of the bar is the total number of SA strains tested that each phage can infect.

In addition, 63% (5/8) of the AB phages were isolation-host specific and 37% (3/8) were not, infecting between 4 and 7 of the AB strains including their host (FIG. 1). 64% (21/33) of the KP phages were isolation-host specific and 36% (12/33) were not, infecting between 2 and 7 of the KP strains including their host (FIG. 2). All of the PA phages were not isolation-host specific; 29% (5/17) of the PA phages infected between 3 and 5 PA strains and 71% (12/17) infected more than 10 strains (FIG. 3). Similarly, all of the SA phages were not isolation-host specific and infected all 16 SA strains (FIG. 4).

Conditional Phage Harvesting

Data indicate that 6 of the 10 KP strains yielded phages with identical host ranges in both conditions: KP01, KP04, KP06, KP08, KP11 and KP12. In addition, 4 of the 10 KP strains yielded phages with conditional dependence: KP03, KP07, KP09 and KP13.

Notably, as determined by host range, KP03, KP09 and KP13 all yielded phages in the presence of FBS that were not found without FBS. Conversely, KP03 and KP07 yielded phages in the absence of FBS that were not found in the presence of FBS. In addition, 5 strains showed conditionally-dependent phage titers: KP03, KP04, KP07, and KP12 showed an apparent increase in phage titer with FBS, while KP06 showed an apparent increase without FBS. Importantly, with all phages found, the isolation condition was not required for infectivity.

Discussion

Data from conditional phage harvesting indicate that varying isolation conditions changes the cohort of the resulting isolated phages from the same water sample. The single sample of environmental water was dived into two portions: (1) one portion was used for traditional phage harvesting in classical TSB culture media, and (2) a second portion was used under identical harvesting conditions, except the second culture also contained 7.5% FBS. The addition of PBS to the second isolation culture was the only difference and both cultures were used to isolate phages against *K. pneumoniae*. Referring to FIG. 5, each row in FIG. 5 corresponds to a single *K. pneumoniae* host strain, and each phage head (hexagon) in the row represents an individual phage isolated against the corresponding strain, +/−FBS (Columns). A critical feature for phage therapeutics is a phage's host range. Phages with different host ranges are functionally different phages, regardless of how similar their genomes are. The number in each phage head in FIG. 5 is the number of different *K. pneumoniae* strains that phage can infect, out of a total of 20 *K. pneumoniae* strains tested. The "+" next to the number indicates that the titer of that isolated phage was increased under that condition with respect to the other condition.

An example of interpreting FIG. 5 is as follows: Against KP01 was found 2 total phages, 1 was found without FBS and 1 was found in the presence of FBS (each column only has 1 phage head). Each phage can only infect KP01 (the number inside each phage head, in each column, is "1"). Thus, these two phages against KP01 are functionally identical. Against KP03 was found 4 total phages (4 phage heads), 2 were found without FBS and 2 were found with FBS. With regard to the two phages with a total host range of 4 (there is a 4 in the phage head), 1 found without FBS and 1 found with FBS, these two phages are functionally the same and have identical host ranges. With respect to the phage with a host range of 3 (there is a 3 inside the phage head), this phage is distinct from the phages with a total host range of 4, and critically was not found in the presence of FBS. Conversely, the phage that only infects KP03 and has a host range of 1 (there is a 1 in the phage head), this phage was found in the presence of FBS and was not found in the absence of FBS.

Importantly, all the phages isolated here, in either condition, were capable of still infecting its host in the other condition, once the phage had been isolated and purified. Additionally, with KP07 for example, the phage with a host range of 4 was isolated a total of twice, as was the KP06 phage with a total host range of 6. Thus such conditionally isolated phages can be found reliably, and NOT in the other condition.

Comparing phage isolation against KP01 and KP03:
(1). some conditional changes do not alter the cohort of isolated phages against a strain.
(2). +/−FBS changed the cohort of phages isolated against KP03 from the exact same water source, with a phage only found in the absence of FBS and a phage only found in the presence of FBS, because of bacterial gene expression and physiological changes between these two conditions.
(3). There are potentially many more phages in the wild that cannot be isolated with traditional cultures and/or there is a competition between phages in isolation cultures.
(4). Varying more features of an isolation culture, according to the specifications of the instant invention here, could potentially yield many more diverse phages and maximize phage isolation. Similarly, if one alters in vivo culture conditions to mirror the host environment, it will be possible to isolate phages better suited to infecting bacteria as they grow during a bona fide infection. Isolating phages using conditional cultures will maximize phage harvesting and phage diversity, with phage diversity being essential for personalized therapeutic cocktail formulation, and having diverse phages will greatly assist other phage therapeutic modalities as well.

Conclusions

Peruvian water sources yielded phages to all pathogens, allowing for the expansion of existing phage libraries against the ESKAPEs. Generally, AB and KP phages isolated here have narrower host ranges than do PA and SA phages. Conditional cultures using FBS can effect phage-yield with respect to the identities of the phages isolated, based on host range, and the amount of the yield (titer) of some phages. Here, +/−FBS allows for the isolation of more diverse phages, even from the exact same environmental water sample. Also, +/−FBS also resulted in both the loss and the gain of isolated phages from different strains, suggesting that conditional cultures can alter bacterial physiology and cause a loss or a gain in phage infectivity.

Taken together, the results suggest that conditional cultures may be used to maximize phage isolation from environmental water sources, resulting in the construction of a more diverse phage library. Moreover, these data suggest that it is possible to use conditional cultures to possibly mirror host-like conditions to force bacterial gene expression and the available receptor repertoire to be more host-adapted-like, and possibly find phages that are better therapeutic candidates. Indeed, even if attempts to mirror in vivo conditions in vitro are never completely successful, data indicate that it is possible to demonstrably alter phage isolation culture conditions so as to enhance (and even possibly maximize) phage isolation from even the exact same environmental water sample and thus build a larger and more diverse and more useful phage library.

Example 2

Conditional Phage Harvesting in the Presence of Host Blood Products

Subsequent to the collection of data described in Example 1, the experimental methods described therein were repeated in another set of experiments with different strains of the same bacterial species and different water samples. Specifically, the method employed was exactly the same as provided above, with the exception that additional cultures containing TSB with 5% sheep blood were also used, in addition to TSB alone and TSB with 7.5% FBS. In addition, some cultures were grown at room temperature.

Details of the experiments performed, and the results obtained in these studies are presented in FIGS. 6, 7, 8A, 8B, 9A, 9B, 10A and 10B. Data in these figures illustrate in numerous bacterial strains and species that the simple addition of PBS or sheep's blood to harvesting cultures not only diversifies phage harvesting across the set of harvesting cultures, but also indicates that there are phages that are conditionally isolated (when scored by host range, arguably the most important feature of a phage with respect to its therapeutic potential), there are phages present in a single sample that can be isolated in the presence of FBS or sheep's blood, that cannot be isolated with media-only traditional cultures, and vice versa. These results illustrate that although these phages are present across the set of cultures via the homogenous aliquoted sample, the conditional cultures produce different "winners" and "losers" from each culture's interphage competition, i.e., "different phage competition outcomes." The exact mechanism as to how these cultures are affecting the bacteria and/or modulating the phage competition outcome is not known, but since the method works in multiple different species, and since in each species the mechanism may vary, the method is nevertheless very robust and likely involves bacterial gene expression differences across the culture set. Future experiments using concentrated mouse organ homogenates (discussed below in Example 3) may improve the ability of conditional culture sets to find even more phages.

Data presented herein indicate that not only are there phages that show conditionally dependent isolation, but there are phages that show conditionally independent and conditionally dependent infection of the same host. For example, FIG. 6 harvesting data with bacterial strain WIQ0239 illustrates that a phage was found against this strain in the presence of sheep's blood, and that this phage cannot infect the WIQ0239 host without sheep's blood present. Also, FIG. 6 harvesting data with bacterial strain WIQ0289 illustrates that there was a phage found that was capable of infecting the WIQ0289 host in traditional culture media and under traditional conditions, but cannot infect when either FBS or sheep's blood is added to the culture. This remarkable result indicates that there are phages in the wild that cannot infect their host strain in the presence of biological materials like FBS and sheep's blood, and there are some phages that are incapable of infecting their host strains in the absence of such biological materials.

The data in FIG. 6 concerning phage against WIQ0289 isolated in traditional media cultures that cannot infect in the presence of FBS or sheep's blood indicate that blood, or a component of blood, blocks phage infectivity in these cultures either directly or by altering bacterial gene expression away from allowing the phage to infect. Thus, it is hypothesized herein that such a phage may show promise in vitro as a potential therapeutic phage, but may fail when used in a host because of serum or blood effects (the mechanism of which may involve direct antagonism at the phage level, or may alter gene expression in the bacteria, or both). This result demonstrates the inherent insufficiency of traditional phage harvesting and the utility of the methods of the instant invention.

Taken together, these data indicate that 1) harvesting cultures contain numerous phages which compete, and that competition can be modulated via changing conditions, allowing for increased phage harvesting from a signal environmental sample when such harvesting is iterated across a set of multiple conditional cultures, and 2) altering bacterial culture conditions, including the addition of host material such as blood or serum, likely changes bacterial gene expression and surface receptor identities effecting phage infectivity. Indeed, bacteria grown under specific culture conditions may not express receptors that are present in other conditions or in vivo, and similarly bacteria in vitro may express surface receptors that are not expressed at all in vivo. Unfortunately, such receptors may act as "decoys" in conventional methods of phage harvesting by selecting for phages that can infect and kill a bacterial strain in vitro, and/or only under certain specific conditions in vitro, and which actually have little therapeutic efficacy on the same bacterial strain in vivo.

Consistent with the data in FIG. 6 concerning *K. pneumoniae* phages, the data in FIGS. 7, 8A, 8B, 9A and 9B illustrate that conditionally dependent phage isolation and conditionally dependent phage infection are also seen in *P. aeruginosa*, again when phage identity is judged by bacterial host range. For example, in FIG. 8B, phages against strain *P. aeruginosa* NSI1489 show conditionally dependent isolation, e.g., the phage isolated from media alone is not found in harvesting cultures containing PBS, and vice versa, and the NSI489 phages also all show conditionally dependent infection, e.g., each phage in that row infects a smaller set of host strains in the presence of blood (bottom ratio), as compared to media alone (top ratio) and media with FBS (middle ratio). Importantly, for example, if one were to assess these phages in vitro in media only cultures for their ability to infect and kill a clinical isolate of interest causing bacteremia in a patient, and thus be used in a phage therapeutic against said bacteremia, the media only results would not predict the performance or accurate host-range of these phages as they infect very differently in the presence of blood. These data suggest that this is a significant weakness of classical phage harvesting and phage host-range determination.

Additionally, FIGS. 7, 8A, 8B, 9A and 9B reveal that there are very different repertoires of phages in the different water samples. For example, the data in FIGS. 7 and 8A show that with those two different water sources, there were no *P. aeruginosa* phages present that could infect the targeted *P. aeruginosa* strains in the presence of FBS. By contrast, FIG. 8B demonstrates that the water source contained no *P. aeruginosa* phages capable of infecting in the presence of sheep blood. Thus, not only do these results demonstrate that conditional phage isolation and conditional phage infection are not phenomena unique to *K. pneumoniae*, as they occur in *P. aeruginosa* as well, indicating that these phenomena are likely generalizable to all bacterial pathogens, but these data also demonstrate the importance of diversifying the environmental sources used for phage isolation.

The data presented in FIGS. 10A and 10B further demonstrates the generalizable phenomena of conditional phage isolation and conditional phage infection with respect to phages against *A. baumannii*. In FIG. 10A, phages against strain WIQ0105 show conditional phage isolation and conditional phage infection.

On the whole, the data presented in FIGS. 6, 7, 8A, 8B, 9A, 9B, 10A and 10B demonstrate that conditionally dependent phage isolation and conditionally dependent phage infection can be seen in *K. pneumoniae*, *P. aeruginosa*, and *A. baumannii*, indicating that conditional effects on phage infection are broadly generalizable.

One can argue that the addition of blood in the cultures creates an environment for the bacteria that is more "host-like." Interestingly, the data indicate that some phages have significantly smaller host ranges in the presence of blood. Thus, the presence of blood in the culture apparently has an impact on the phages, the bacteria, or both, which can change phage infectivity. A very reasonable explanation is that some of the host bacteria change gene expression in the presence of blood and that changes phage infection dynamics.

In addition, data indicate that with a particular water sample, phages could not be isolated against any of the bacterial host strains in the presence of serum, but it was possible in media. Presumably none of the media harvested phages will infect under certain conditions in the presence of host material like serum. Thus, these data suggest that traditional studies using conventional media only infection and harvesting conditions may lead to over-predictions with regard to phage infectivity in vivo.

Significantly, taken together, the data support the concept disclosed herein that aliquoting a sample comprising phages across a set of cultures that conditionally vary, and thereby modulating phage competition outcomes across the set, optimizes and enhances phage harvesting from a single environmental source and allows the recovery of phages from that sample that cannot be found otherwise, likely because the same bacteria strain is expressing different surface features across the set of conditional harvesting cultures. Thus, in effect, the bacteria are literally different across the set of cultures with respect to phage harvesting.

Example 3

Experiments Using Concentrated Mouse Organ Homogenates

Various possible culture features and additives may be employed in the methods of the invention. For example, future experiments involving creating different culture conditions comprising using various concentrated mouse organ homogenates are contemplated herein. These experiments may be performed as follows.

Materials and Methods:

Homogenates of various mouse tissues have been prepared. Specifically, livers, spleens, kidneys, hearts, and brains from uninfected BALB/c mice have been prepared by pooling said organs from over 50 mice and homogenizing the material into 50 ml PBS, pH 7.2.

Whole mouse organs, including liver, brain, heart, spleen, kidney, muscle tissue, and bone, homogenized together or separately in PBS, could be added in various concentrations (e.g. 5%-25%) to phage harvesting cultures. These homogenates will contain very complex mixtures of host-derived materials in solution as well as insoluble materials that could provide host-specific surfaces. It is contemplated herein that using the general methods described above for phage harvesting, but using harvesting cultures that contain these kinds of mouse organ homogenates, will be superior to FBS and/or blood at mimicking the host environment and producing host-adapted bacteria in said harvesting cultures.

In a particular embodiment, it is proposed that these homogenates may be utilized in additional future experiments according to the methods of the invention as proposed below. Phage harvesting according to the methods of the instant invention, specifically as performed and data presented in FIGS. 6, 7, 8A, 8B, 9A, 9B, 10A, and 10B, will be repeated with fresh environmental water samples but now with a fourth condition. Thus, in addition to media, media+7.5% FBS, and media+5% sheep blood, a harvesting culture comprising media+5% of the moue organ homogenate described above will be used. Such a strategy using all four conditions will allow for comparisons across all the conditions, looking for changes in or enhancements of conditional phage isolation and/or conditional phage infection in the presence of mouse organ homogenates. It is also contemplated herein that a fifth conditional harvesting culture may also be generated that contains all of the additives, e.g. FBS, sheep blood, as well as mouse organ homogenates. Such a culture may prove to be superior to all previously tested conditions.

What is claimed is:

1. A method of enhancing harvesting of phages against a targeted host bacteria from a sample comprising phages, comprising culturing aliquots of said sample in a plurality of in vitro cultures comprising said targeted host bacteria in various concentrations of homogenates of mammalian organ, muscle, and bone.

2. The method of claim 1, wherein said culturing step produces one or more changes in the targeted host bacteria that occurs in vivo during host-adaptation.

3. A method of identifying phages with enhanced propensity to infect and kill an infectious pathogenic bacteria in vivo, comprising:
   a. culturing the infectious pathogenic bacteria in a plurality of in vitro cultures comprising various concentrations of homogenates of mammalian organ, muscle, and bone;
   b. culturing a sample comprising phages in said plurality of in vitro cultures from step a; and
   c. assaying said plurality of in vitro cultures to identify phages that can infect and kill the infectious pathogenic bacteria in vitro in said various concentrations of homogenates of mammalian organ, muscle and bone.

4. The method of claim 2 or claim 3, wherein said culturing produces changes in expression of one or more genes encoding bacterial surface features used as phage receptors.

5. The method of claim 1 or claim 3, wherein the sample comprising phages comprises one or more phages found in nature.

6. The method of claim 1 or claim 3, wherein the sample comprising phages is collected from one or more natural and/or man-made sources.

7. The method of claim 6, wherein said one or more natural and/or man-made sources is selected from the group consisting of soil, water treatment plants, raw sewage, sea water, lakes, rivers, streams, cesspools, animal intestines, human intestines, manure or other fecal matter, organic substrates, biofilms, and medical/hospital sources.

8. The method of claim 1 or claim 3, wherein the culturing is under further various conditions selected from the group consisting of temperature, time, osmotic pressure, pH, $CO_2$ percentage, $O_2$ percentage, nutrient concentration(s), carbon source(s), carbon source concentration(s), growth factor concentration(s), hormone concentration(s), in vitro culture surface characteristics, and concentration of inducer(s) of bacterial virulence factors.

9. The method of claim 8, wherein the nutrients are selected from the group consisting of amino acids, carbohydrates, vitamins, and minerals.

10. The method of claim 1 or claim 3, wherein the mammalian organ, muscle, and bone are from a mouse.

11. The method of claim 1 or claim 3, wherein the various concentrations of homogenates of mammalian organ, muscle, and bone are 5-25% by weight of said plurality of in vitro cultures.

12. The method of claim 1 or claim 3, wherein the organ is selected from the group consisting of liver, brain, heart, spleen, and kidney.

13. The method of claim 1 or claim 3, wherein the plurality of in vitro cultures further comprise one or more additional culture additives selected from the group consisting of whole or fractionated mammalian serum, whole or fractionated mammalian plasma, and whole mammalian blood.

14. The method of claim 13, wherein said whole or fractionated mammalian serum is selected from the group consisting of human serum, animal serum, and a combination thereof.

15. The method of claim 13, wherein said whole or fractionated mammalian serum is added to said plurality of in vitro cultures at a concentration of 0-15%.

16. The method of claim 15, wherein the concentration is 7.5%.

17. The method of claim 14, wherein the animal serum is fetal bovine serum (FBS).

18. The method of claim 13, wherein said whole or fractionated mammalian plasma is selected from the group consisting of human plasma, animal plasma, and a combination thereof.

19. The method of claim 13, wherein said whole or fractionated mammalian plasma is added to said plurality of in vitro cultures at a concentration of 0-15%.

20. The method of claim 19 wherein the concentration is 7.5%.

21. The method of claim 13, wherein said whole mammalian blood is selected from the group consisting of human blood, animal blood, and a combination thereof.

22. The method of claim 13, wherein said whole mammalian blood is added to said plurality of in vitro cultures at a concentration of 0-15%.

23. The method of claim 22, wherein the concentration is 5%.

24. The method of claim 21, wherein the animal blood is sheep blood.

25. The method of claim 13, wherein said fractionated mammalian serum and said fractionated mammalian plasma may be fractionated by heat, centrifugation, or biochemically using column chromatography prior to addition to the plurality of in vitro cultures.

26. The method of claim 13 wherein said whole or fractionated mammalian serum and said whole or fractionated mammalian plasma may or may not be heat inactivated.

27. The method of claim 9, wherein the minerals are selected from the group consisting of iron and magnesium.

* * * * *